(12) United States Patent
Konetzki et al.

(10) Patent No.: US 7,709,474 B2
(45) Date of Patent: *May 4, 2010

(54) ENANTIOMERICALLY PURE BETA AGONISTS, MANUFACTURING AND USE THEREOF

(75) Inventors: Ingo Konetzki, Warthausen (DE); Peter Sieger, Mittelbiberach (DE)

(73) Assignee: Boehringer Ingelheim International GmbH, Ingelheim (DE)

( * ) Notice: Subject to any disclaimer, the term of this patent is extended or adjusted under 35 U.S.C. 154(b) by 0 days.

This patent is subject to a terminal disclaimer.

(21) Appl. No.: 11/842,485

(22) Filed: Aug. 21, 2007

(65) Prior Publication Data

US 2008/0070909 A1  Mar. 20, 2008

(30) Foreign Application Priority Data

Aug. 22, 2006  (EP) .................... 06119273

(51) Int. Cl.
C07D 265/36 (2006.01)
A61K 31/536 (2006.01)
(52) U.S. Cl. .................... 514/229.5; 544/92
(58) Field of Classification Search ............ 544/92; 514/229.5
See application file for complete search history.

(56) References Cited

U.S. PATENT DOCUMENTS

| | | | |
|---|---|---|---|
| 4,341,778 | A | 7/1982 | Mentrup et al. |
| 4,460,581 | A | 7/1984 | Schromm et al. |
| 4,570,630 | A | 2/1986 | Elliot et al. |
| 4,950,767 | A | 8/1990 | Kraatz |
| 7,160,882 | B2 | 1/2007 | Bouyssou et al. |
| 7,220,742 | B2 | 5/2007 | Lustenberger et al. |
| 2006/0189605 | A1 | 8/2006 | Konetzki et al. |
| 2007/0027148 | A1 | 2/2007 | Lustenberger et al. |
| 2007/0066607 | A1 | 3/2007 | Fairhurst et al. |
| 2007/0112191 | A1 | 5/2007 | Santagostino et al. |
| 2008/0051392 | A1 | 2/2008 | Konetzki et al. |
| 2008/0053430 | A1 | 3/2008 | Nowak et al. |
| 2009/0105236 | A1 | 4/2009 | Konetzki et al. |

FOREIGN PATENT DOCUMENTS

| | | |
|---|---|---|
| CA | 2 164 222 C | 12/1994 |
| CA | 2 232 151 C | 4/1997 |
| CA | 2 233 981 C | 4/1997 |
| CA | 2 237 853 C | 6/1997 |
| CA | 2 300 908 A1 | 4/1999 |
| CA | 2 450 961 A1 | 1/2003 |
| CA | 2 425 539 A1 | 4/2003 |
| CA | 2 425 560 A1 | 4/2003 |
| CA | 2 471 578 A1 | 8/2003 |
| CA | 2 472 149 A1 | 8/2003 |
| CA | 2 474 874 A1 | 8/2003 |
| CA | 2 552 784 A1 | 8/2005 |
| CA | 2 562 859 A1 | 11/2005 |
| DE | 36 09 152 A1 | 9/1987 |
| EP | 0 043 940 A1 | 1/1982 |
| EP | 0 237 507 A1 | 9/1987 |
| WO | 91/14468 A1 | 10/1991 |
| WO | 94/07607 A1 | 4/1994 |
| WO | 94/28958 A1 | 12/1994 |
| WO | 95/32937 A1 | 12/1995 |
| WO | 97/12683 A1 | 4/1997 |
| WO | 97/12687 A1 | 4/1997 |
| WO | 97/20590 A1 | 6/1997 |
| WO | 99/16530 A1 | 4/1999 |
| WO | 02/30928 A1 | 4/2002 |
| WO | 02/32898 A2 | 4/2002 |
| WO | 03/000265 A1 | 1/2003 |
| WO | 03/064417 A1 | 8/2003 |
| WO | 03/064418 A1 | 8/2003 |
| WO | 03/064419 A1 | 8/2003 |
| WO | 2004/087142 A1 | 10/2004 |
| WO | 2005/070908 A1 | 8/2005 |
| WO | 2005/111005 A1 | 11/2005 |
| WO | 2006/089859 A1 | 8/2006 |

OTHER PUBLICATIONS

Vippagunta et al, "Crystalline Solids" Advanced Drug Delivery Reviews, vol. 48, pp. 3-26 (2001).*
Gavezzotti, "Are Crystal Structures Predictable?" Accounts of Chemical Research, vol. 27, pp. 309-314 (1994).*
See R. S. Bedi, Inhaled Corticosteroids in COPD, Indian J. Chest Dis. Allied Sci. 2005; 47:243-244.*
International Search Report and Written Opinion for PCT/EP2006/068157 mailed on Apr. 16, 2007.
International Search Report for PCT/EP2007/058653 mailed Oct. 29, 2007.

(Continued)

Primary Examiner—Kahsay T Habte
(74) Attorney, Agent, or Firm—Michael P. Morris; Mary-Ellen M. Devlin; Edouard G. Lebel

(57) ABSTRACT

The present invention relates to enantiomerically pure compounds of formula 1

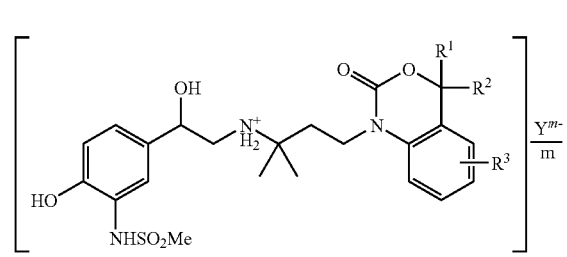

wherein the groups $R^1$, $R^2$, $R^3$, m and $Y^{m-}$ may have the meanings given in the claims and specification, processes for preparing them and their use as medicaments, particularly as medicaments for the treatment of respiratory complaints.

16 Claims, 6 Drawing Sheets

OTHER PUBLICATIONS

Figure 1:
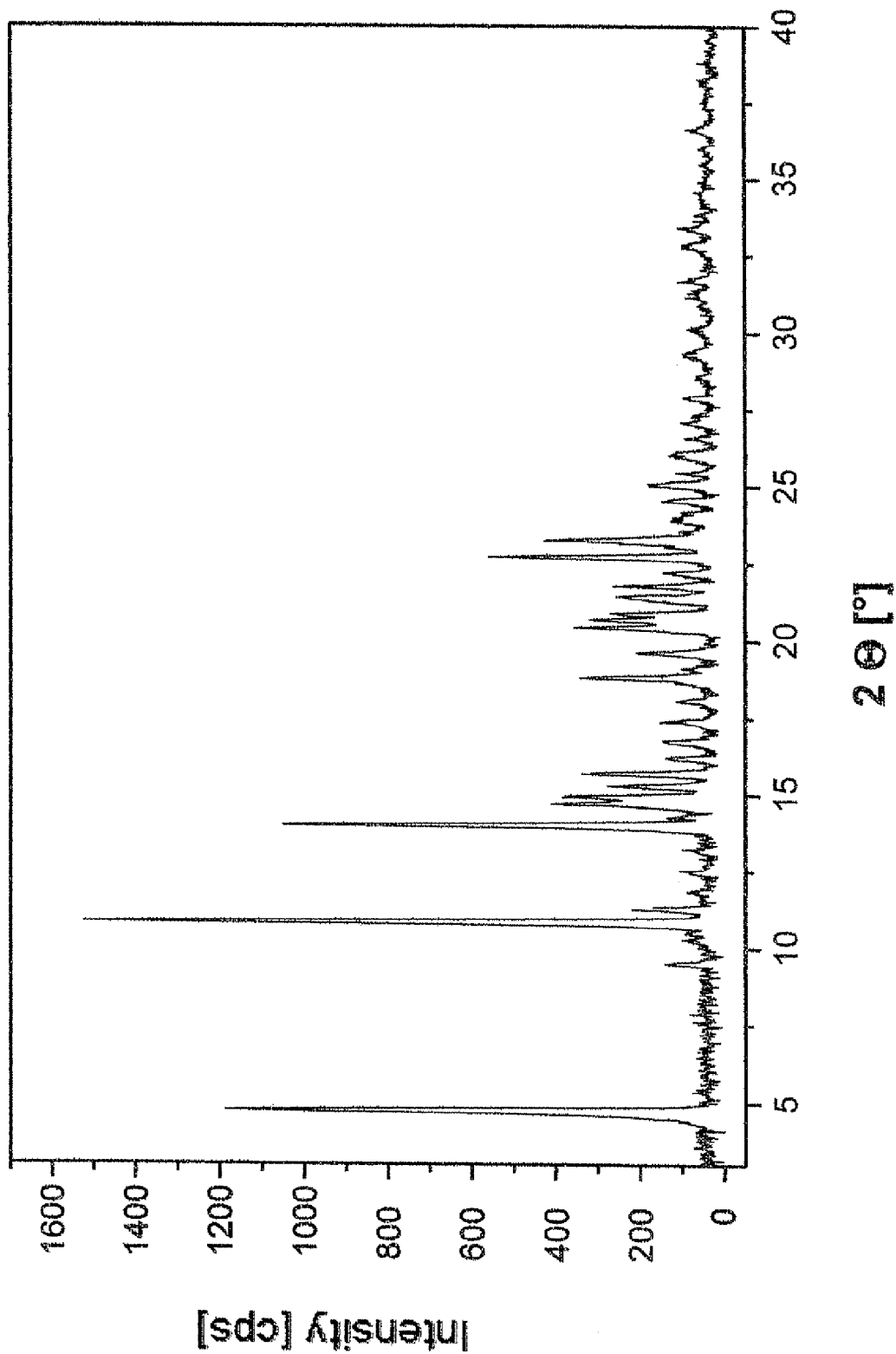

International Search Report for PCT/EP2007/058654 mailed Dec. 6, 2007.
International Search Report for PCT/EP2007/058655 mailed Oct. 29, 2007.
International Search Report for PCT/EP2006/060033 mailed May 4, 2006.
E.J. Corey; Reduction of Carbonyl Compounds with Chiral Oxazaborolidine Catalysts: A New Paradigm for Enantioselective Catalysis and a Powerful New Synthetic Method; Angew. Chem. Int. Ed, 1998, vol. 37 pp. 1986-2012.
Y.Hong; cis-1-Amino-2-indanol in Asymmetric Synthesis, Part I. A Practical Catalyst System for the Enantioselective Borane Reduction of Aromatic Ketones; Tetrahedron Lett., 1994, vol. 35, No. 36 pp. 6631-6634; Great Britain.
S. Itsuno; Asymmetric Reduction of Aliphatic Ketones with the Reagent Prepared from (S)-(−)-2-Amino-3methyl-1-1,1-diphenylbutan-1-ol and Borane; J. Org. Chem (1984) vol. 49 pp. 555-557.
G.J. Quallich; Diphenyloxazaborolidine A New Catalyst for Enantioselective Reduction of Ketones;Tetrahedron Lett (1993) vol. 34 No. 26 pp. 4145-4148; Great Britain.
S. Itsuno; Asymmetric Synthesis Using Chirally Modified Borohydrides, Part 1. Enantioselective Reduction of Aromatic Ketones with the Reagent Prepared from Borane and (S)-Valinol; J. Chem. Soc. Perkin Trans. I (1983) pp. 1673-1676.
R. Hett et al; Conformational Toolbox of Oxazaborolidine Catalysts in the Enantioselective Reduction of a-Bromo-Ketone for the Synthesis of (R,R)-Formoterol;Tetrahedron Letters (1998) vol. 39 pp. 1705-1708.
A. Hirao; Asymmetric Reduction of Aromatic Ketones with Chiral Alkoxy-amine-borane Complexes; J. Chem. Soc. Chem.Comm (1981) pp. 315-317.
G. J. Quallich; In Situ Oxazaborolidines, Practical Enantioselective Hydride Reagents;Synlett, Dec. 1993, p. 929.
M. Masui; A Practical Method for Asymmetric Borane Reduction of Prochiral Ketones Using Chiral Amino Alcohols and Trimethyl Borate; Synlett, Mar. 1997, pp. 273-274.
T. Hamada; Practical Synthesis of Optically Active Styrene Oxides via Reductive Transformation of 2-chloroacetophenones with Chiral Rhodium Catalysts; Org. Lett (2002) vol. 4 No. 24 pp. 4373-4376.
J. Chandrasekharan; The Reduction of Oximes by Lithium Aluminum Hydride in Hexamethylphosphoramide Solvent; J. Org. Chem (1985) vol. 50 pp. 5448-5450.
J.S. Lodaya; Direct a-Mesyloxylation of Ketones and b-dicarbonyl Compounds with [Hydroxy(mesyloxy)iodo] benzene; J. Org. Chem (1988) vol. 53 p. 210.
K.Yutaka; 2-Amino-4-phenylthiazole derivatives as anti-atherogenic agents; Eur. J. Med. Chem. Chim.Ther (1981) vol. 16 pp. 355-362.
S. Kajigaeshi; z-Chloroination of Aromatic Acetyl Derivatives with Benzyltrimethylammonium Dichloroiodate; Synthesis Jul. 1988, vol. 7, pp. 545-546.
E. Vedejs; A Tyrosine-Derived Benzofuranone Related to a Diazonamide A; Org. Lett (2000) vol. 2 No. 8 pp. 1031-1032.
A. Guy; Selective a-Chloroination of Alkyl Aryl Ketones; Synthesis 1982, 12, pp. 1018-1020.
A. V. Rama Rao et al; Enantioselective Catalytic reductions Of Ketones with New Four Membered Oxazaborolidines: Application to (S)- Tetramisole; Tetrahedron: Asymmetry (1992) vol. 3 No. 7 pp. 859-862; Elsevier Science Publisher.
Gerald F. Koser et al; One-Step Alpha-Tosyloxylation of Ketones with [Hydeoxy(tosyloxy)iodo]Benzene; Journal of Organic Chemistry (1982) vol. 47 No. 12 pp. 2487-2489.
Jonathan D. Bloom et al; Disodium (R,R)-5[2-[[2-(3Chlorophenyl)-2-hydroxyethyl]-amino]propyl]-1,3-benzodloxole-2,2-dicarboxylate (CL 316,243). A Potent Beta-Adrenergic Agonist Virtually Specific for Beta2 Receptors. A Promising Antidiabetic and Antiobesity Agent; Journal of medicinal Chemistry (1992) vol. 35 No. 16 pp. 3081-3084.
Paula Yurkanis Bruice; Glossary: Organic Chemistry (1995) p. G-7.

* cited by examiner

ENANTIOMERICALLY PURE BETA AGONISTS, MANUFACTURING AND USE THEREOF

This application claims priority benefit from EP 06 119 273.8, filed Aug. 22, 2006, which is incorporated herein in its entirety.

The present invention relates to enantiomerically pure compounds of formula 1

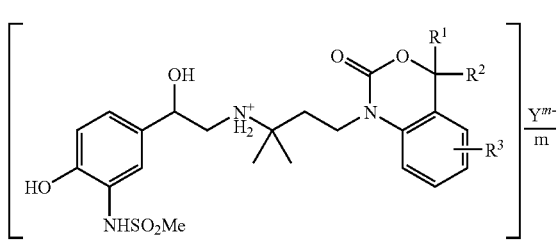

wherein the groups $R^1$, $R^2$, $R^3$, m and $Y^{m-}$ may have the meanings given in the claims and specification, processes for preparing them and their use as medicaments, particularly as medicaments for the treatment of respiratory complaints.

BACKGROUND TO THE INVENTION

Betamimetics (β-adrenergic substances) are known from the prior art. In this respect reference may be made for example to the disclosure of U.S. Pat. No. 4,341,778 which proposes betamimetics for the treatment of a wide range of ailments.

For drug treatment of diseases it is often desirable to prepare medicaments with a longer duration of activity. As a rule, this ensures that the concentration of the active substance in the body needed to achieve the therapeutic effect is maintained for a longer period without the need to re-administer the drug at frequent intervals. Moreover, giving an active substance at longer time intervals contributes to the well-being of the patient to a high degree.

It is particularly desirable to prepare a pharmaceutical composition which can be used therapeutically by administration once a day (single dose). The use of a drug once a day has the advantage that the patient can become accustomed relatively quickly to regularly taking the drug at certain times of the day.

The aim of the present invention is therefore to provide betamimetics which on the one hand provide a therapeutic benefit in the treatment of respiratory complaints and are also characterised by a longer duration of activity and can thus be used to prepare pharmaceutical compositions with a longer duration of activity. A particular aim of the invention is to prepare betamimetics which, by virtue of their long-lasting effect, can be used to prepare a drug for the treatment of asthma for administration once a day. In addition to these aims, a further objective of the invention is to provide such betamimetics which are not only exceptionally potent but are also characterised by a high degree of selectivity with respect to the β$_2$-adreno-receptor. A further aim of the present invention is to provide betamimetics which by virtue of their physicochemical properties can be used especially for the preparation of pharmaceutical formulations that are particularly suitable for use by inhalation. In particular, the present invention sets out to provide betamimetics which in addition to having the above-mentioned properties are also particularly suitable for the production of inhalable powders and suspension aerosols.

DETAILED DESCRIPTION OF THE INVENTION

Surprisingly it has been found that the abovementioned problems are solved by compounds of general formula 1. The present invention relates to enantiomerically pure compounds of formula 1

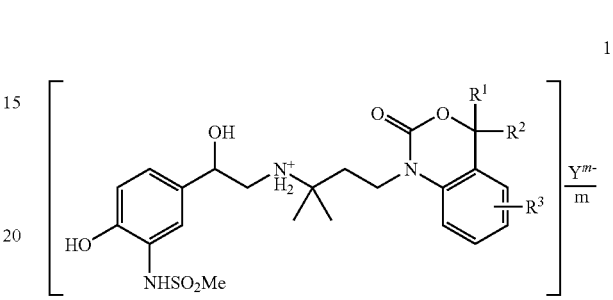

wherein
$R^1$ and $R^2$ independently of one another denote H, halogen or $C_{1-4}$-alkyl or together denote $C_{1-6}$-alkylene; and
$R^3$ denotes H, halogen, OH, $C_{1-4}$-alkyl or O—$C_{1-4}$-alkyl;
$Y^{m-}$ denotes an anion with m negative charges preferably selected from among chloride, bromide, iodide, sulphate, phosphate, methanesulphonate, nitrate, maleinate, acetate, benzoate, citrate, salicylate, trifluoroacetate, fumarate, tartrate, oxalate, succinate, ethanedisulphonate, propanedisulphonate, benzoate and p-toluenesulphonate;
m denotes 1 or 2;

optionally in the form of the tautomers, mixtures of the tautomers, hydrates or solvates thereof.

The compounds of formula 1 consist of a molecule with a single positive charge and an anion $Y^{m-}$ with a single charge or a corresponding 1/m share of an anion $Y^{m-}$ with m charges. Thus, for example, two molecules of formula

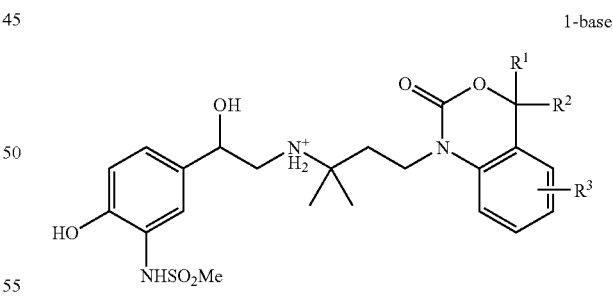

1-base wherein the groups $R^1$, $R^2$ and $R^3$ may have the above meanings, may be present in a crystalline union with a doubly charged anion $Y^{m-}$ wherein m=2, such as e.g. ethanedisulphonate or propanedisulphonate.

Preferred are compounds of formula 1 as described above in the form of the enantiomerically pure compounds, while the R-enantiomers of the compounds of formula 1 according to the invention are of exceptional importance. The R-enantiomers of the compounds of formula 1 can be represented by general formula R-1

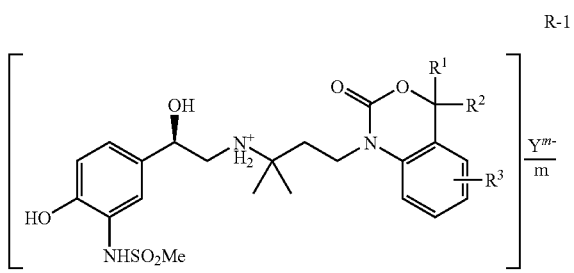

R-1 wherein the groups $R^1$, $R^2$, $R^3$, m and $Y^{m-}$ may have the meanings given above. The (R)- and (S)-enantiomers may be obtained by common methods known in the art.

Preferred are enantiomerically pure compounds of formula 1, wherein $R^1$ and $R^2$ which may be identical or different, denote hydrogen, fluorine, chlorine, methyl, ethyl, propyl, butyl or together denote —$CH_2$—$CH_2$—, —$CH_2$—$CH_2$—$CH_2$—, —$CH_2$—$CH_2$—$CH_2$—$CH_2$— or —$CH_2$—$CH_2$—$CH_2$—$CH_2$—$CH_2$—;

$R^3$ denotes hydrogen, fluorine, chlorine, OH, methyl, ethyl, methoxy, or ethoxy $Y^{m-}$ denotes an anion with m negative charges, preferably an anion with m negative charges selected from among chloride, bromide, iodide, sulphate, phosphate, methanesulphonate, nitrate, maleinate, acetate, benzoate, citrate, salicylate, trifluoroacetate, fumarate, tartrate, oxalate, succinate, ethanedisulphonate, benzoate and p-toluenesulphonate;

m denotes 1 or 2;

optionally in the form of the tautomers, mixtures of the tautomers, hydrates or solvates thereof.

Preferred are enantiomerically pure compounds of formula 1, wherein $R^1$ and $R^2$ which may be identical or different, denote hydrogen, methyl, ethyl, propyl or together denote —$CH_2$—$CH_2$—, —$CH_2$—$CH_2$—$CH_2$—, —$CH_2$—$CH_2$—$CH_2$—$CH_2$— or —$CH_2$—$CH_2$—$CH_2$—$CH_2$—$CH_2$—;

$R^3$ denote hydrogen, fluorine, OH, methyl or methoxy;

$Y^{m-}$ denotes an anion with m negative charges, preferably an anion with m negative charges selected from among chloride, bromide, iodide, sulphate, phosphate, methanesulphonate, nitrate, maleinate, acetate, benzoate, citrate, salicylate, trifluoroacetate, fumarate, tartrate, oxalate, succinate, ethanedisulphonate, benzoate and p-toluenesulphonate;

m denotes 1 or 2;

optionally in the form of the tautomers, mixtures of the tautomers, hydrates or solvates thereof.

Preferred are enantiomerically pure compounds of formula 1, wherein $R^1$ and $R^2$ which may be identical or different, denote ethyl, propyl or together denote —$CH_2$—$CH_2$—, —$CH_2$—$CH_2$—$CH_2$—, —$CH_2$—$CH_2$—$CH_2$—$CH_2$— or —$CH_2$—$CH_2$—$CH_2$—$CH_2$—$CH_2$—;

$R^3$ represents hydrogen, fluorine, OH, methyl or methoxy.

$Y^{m-}$ denotes an anion with m negative charges, preferably an anion with m negative charges selected from among chloride, bromide, iodide, sulphate, phosphate, methanesulphonate, nitrate, maleinate, acetate, benzoate, citrate, salicylate, trifluoroacetate, fumarate, tartrate, oxalate, succinate, ethanedisulphonate, benzoate and p-toluenesulphonate;

m denotes 1 or 2;

optionally in the form of the tautomers, mixtures of the tautomers, hydrates or solvates thereof.

Preferred are enantiomerically pure compounds of formula 1, wherein $R^1$ and $R^2$ denote ethyl, propyl or together denote —$CH_2$—$CH_2$—, —$CH_2$—$CH_2$—$CH_2$—, —$CH_2$—$CH_2$—$CH_2$—$CH_2$— or —$CH_2$—$CH_2$—$CH_2$—$CH_2$—$CH_2$—;

$R^3$ represents hydrogen, fluorine, OH or methoxy.

$Y^{m-}$ denotes an anion with m negative charges, preferably an anion with m negative charges selected from among chloride, bromide, iodide, sulphate, phosphate, methanesulphonate, nitrate, maleinate, acetate, benzoate, citrate, salicylate, trifluoroacetate, fumarate, tartrate, oxalate, succinate, ethanedisulphonate, benzoate and p-toluenesulphonate;

m denotes 1 or 2;

optionally in the form of the tautomers, mixtures of the tautomers, hydrates or solvates thereof.

Preferred are the following enantiomerically pure compounds of formula 1.1: N-(5-{2-[1,1-dimethyl-3-(4-methyl-2-oxo-4H-benzo[d][1,3]oxazin-1-yl)-propylamino]-1-hydroxy-ethyl}-2-hydroxy-phenyl)-methanesulphonamide*H($Y^{m-}$/m)

1.2: N-(5-{2-[1,1-dimethyl-3-(2-oxo-4H-benzo[d][1,3]oxazin-1-yl)-propylamino]-1-hydroxy-ethyl}-2-hydroxy-phenyl)-methanesulphonamide*H($Y^{m-}$/m)

1.3: N-(5-{2-[3-(4-ethyl-2-oxo-4H-benzo[d][1,3]oxazin-1-yl)-1,1-dimethyl-propylamino]-1-hydroxy-ethyl}-2-hydroxy-phenyl)-methanesulphonamide*H($Y^{m-}$/m)

1.4: N-(5-{2-[3-(4,4-dimethyl-2-oxo-4H-benzo[d][1,3]oxazin-1-yl)-1,1-dimethyl-propylamino]-1-hydroxy-ethyl}-2-hydroxy-phenyl)-methanesulphonamide*H($Y^{m-}$/m)

1.5: N-(2-hydroxy-5-{1-hydroxy-2-[3-(6-hydroxy-4,4-dimethyl-2-oxo-4H-benzo[d][1,3]oxazin-1-yl)-1,1-dimethyl-propylamino]-ethyl}-phenyl)-methanesulphonamide*H($Y^{m-}$/m)

1.6: N-(2-hydroxy-5-{1-hydroxy-2-[3-(6-methoxy-4,4-dimethyl-2-oxo-4H-benzo[d][1,3]oxazin-1-yl)-1,1-dimethyl-propylamino]-ethyl}-phenyl)-methanesulphonamide*H($Y^{m-}$/m)

1.7: N-(5-{2-[1,1-dimethyl-3-(2-oxo-4,4-dipropyl-4H-benzo[d][1,3]oxazin-1-yl)-propylamino]-1-hydroxy-ethyl}-2-hydroxy-phenyl)-methanesulphonamide*H($Y^{m-}$/m)

1.8: N-[5-(2-{1,1-dimethyl-3-[spiro(cyclohexane-1,4'-2H-3',1'-benzoxazin)-2'-oxo-1-yl]-propylamino}-1-hydroxy-ethyl)-2-hydroxy-phenyl]-methanesulphonamide*H($Y^{m-}$/m)

1.9: N-[5-(2-{1,1-dimethyl-3-[spiro(cyclopropyl-1,4'-2H-3',1'-benzoxazin)-2'-oxo-1-yl]-propylamino}-1-hydroxy-ethyl)-2-hydroxy-phenyl]-methanesulphonamide*H($Y^{m-}$/m)

1.10: N-(5-{2-[3-(4,4-diethyl-2-oxo-4H-benzo[d][1,3]oxazin-1-yl)-1,1-dimethyl-propylamino]-1-hydroxy-ethyl}-2-hydroxy-phenyl)-methanesulphonamide*H($Y^{m-}$/m)

1.11: N-(5-{2-[3-(4,4-diethyl-6-fluoro-2-oxo-4H-benzo[d][1,3]oxazin-1-yl)-1,1-dimethyl-propylamino]-1-hydroxy-ethyl}-2-hydroxy-phenyl)-methanesulphonamide*H($Y^{m-}$/m)

1.12: N-(5-{2-[3-(4,4-diethyl-7-fluoro-2-oxo-4H-benzo[d][1,3]oxazin-1-yl-1,1-dimethyl-propylamino]-1-hydroxy-ethyl}-2-hydroxy-phenyl)-methanesulphonamide*H(Y$^{m-}$/m)

1.13: N-(5-{2-[3-(4,4-diethyl-8-methoxy-2-oxo-4H-benzo[d][1,3]oxazin-1-yl)-1,1-dimethyl-propylamino]-1-hydroxy-ethyl}-2-hydroxy-phenyl)-methanesulphonamide*H(Y$^{m-}$/m)

1.14: N-(5-{2-[3-(4,4-diethyl-6-methoxy-2-oxo-4H-benzo[d][1,3]oxazin-1-yl)-1,1-dimethyl-propylamino]-1-hydroxy-ethyl}-2-hydroxy-phenyl)-methanesulphonamide*H(Y$^{m-}$/m)

wherein

Y$^{m-}$ denotes an anion with m negative charges, preferably an anion with m negative charges selected from among chloride, bromide, iodide, sulphate, phosphate, methanesulphonate, nitrate, maleinate, acetate, benzoate, citrate, salicylate, trifluoroacetate, fumarate, tartrate, oxalate, succinate, ethanedisulphonate, benzoate and p-toluenesulphonate;

m denotes 1 or 2;

optionally in the form of the tautomers, mixtures of the tautomers, hydrates or solvates thereof.

Particularly preferred are enantiomerically pure compounds of formula 1.7: N-(5-{2-[1,1-dimethyl-3-(2-oxo-4,4-dipropyl-4H-benzo[d][1,3]oxazin-1-yl)-propylamino]-1-hydroxy-ethyl}-2-hydroxy-phenyl)-methanesulphonamide*H(Y$^{m-}$/m)

1.8: N-[5-(2-{1,1-dimethyl-3-[spiro(cyclohexane-1,4'-2H-3',1'-benzoxazin)-2'-oxo-1-yl]-propylamino}-1-hydroxy-ethyl)-2-hydroxy-phenyl]-methanesulphonamide*H(Y$^{m-}$/m)

1.9: N-[5-(2-{1,1-dimethyl-3-[spiro(cyclopropyl-1,4'-2H-3',1'-benzoxazin)-2'-oxo-1-yl]-propylamino}-1-hydroxy-ethyl)-2-hydroxy-phenyl]-methanesulphonamide*H(Y$^{m-}$/m)

1.10: N-(5-{2-[3-(4,4-diethyl-2-oxo-4H-benzo[d][1,3]oxazin-1-yl)-1,1-dimethyl-propylamino]-1-hydroxy-ethyl}-2-hydroxy-phenyl)-methanesulphonamide*H(Y$^{m-}$/m)

1.11: N-(5-{2-[3-(4,4-diethyl-6-fluoro-2-oxo-4H-benzo[d][1,3]oxazin-1-yl)-1,1-dimethyl-propylamino]-1-hydroxy-ethyl}-2-hydroxy-phenyl)-methanesulphonamide*H(Y$^{m-}$/m)

1.12: N-(5-{2-[3-(4,4-diethyl-7-fluoro-2-oxo-4H-benzo[d][1,3]oxazin-1-yl-1,1-dimethyl-propylamino]-1-hydroxy-ethyl}-2-hydroxy-phenyl)-methanesulphonamide*H(Y$^{m-}$/m)

1.13: N-(5-{2-[3-(4,4-diethyl-8-methoxy-2-oxo-4H-benzo[d][1,3]oxazin-1-yl)-1,1-dimethyl-propylamino]-1-hydroxy-ethyl}-2-hydroxy-phenyl)-methanesulphonamide*H(Y$^{m-}$/m)

1.14: N-(5-{2-[3-(4,4-diethyl-6-methoxy-2-oxo-4H-benzo[d][1,3]oxazin-1-yl)-1,1-dimethyl-propylamino]-1-hydroxy-ethyl}-2-hydroxy-phenyl)-methanesulphonamide*H(Y$^{m-}$/m)

wherein

Y$^{m-}$ denotes an anion with m negative charges, preferably an anion with m negative charges selected from among chloride, bromide, iodide, sulphate, phosphate, methanesulphonate, nitrate, maleinate, acetate, benzoate, citrate, salicylate, trifluoroacetate, fumarate, tartrate, oxalate, succinate, ethanedisulphonate, benzoate and p-toluenesulphonate;

m denotes 1 or 2;

optionally in the form of the tautomers, mixtures of the tautomers, hydrates or solvates thereof.

Particularly preferred are enantiomerically pure compounds of formula 1, wherein the groups R$^1$, R$^2$ and R$^3$ may have the above mentioned meanings and wherein Y$^{m-}$ denotes chloride or bromide, optionally in the form of the tautomers, mixtures of the tautomers, hydrates or solvates thereof.

Particularly preferred are enantiomerically pure compounds of formula n 1.1 to 1.14, wherein Y$^{m-}$ denotes chloride or bromide, optionally in the form of the tautomers, mixtures of the tautomers, hydrates or solvates thereof.

Particularly preferred are enantiomerically pure compounds of formula 1.7 to 1.14, wherein Y$^{m-}$ denotes chloride or bromide, optionally in the form of the tautomers, mixtures of the tautomers, hydrates or solvates thereof.

Also particularly preferred are the above enantiomerically pure compounds of general formula 1 in crystalline form, optionally in the form of the crystalline tautomers, crystalline hydrates or crystalline solvates thereof. Particularly preferred are the above enantiomerically pure, crystalline compounds of general formula 1 optionally in the form of the crystalline tautomers, crystalline hydrates or crystalline solvates thereof, which are further characterised in that they are crystalline compounds that are present in a single crystal modification.

By the term "single crystal modification" are meant crystalline compounds of formula 1 that do not constitute a mixture of any existing crystal modifications.

In another aspect the invention relates to enantiomerically pure, solvent-free, crystalline forms of compounds of formula 1-base

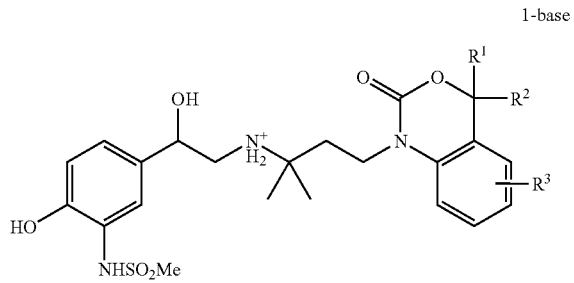

1-base wherein

R$^1$ and R$^2$ which may be identical or different, preferably identical, denote ethyl or propyl, or together denote —CH$_2$—CH$_2$—, —CH$_2$—CH$_2$—CH$_2$—, —CH$_2$—CH$_2$—CH$_2$—CH$_2$— or —CH$_2$—CH$_2$—CH$_2$—CH$_2$—CH$_2$— and R$^3$ denotes hydrogen, fluorine, chlorine, OH, methyl, ethyl, methoxy or ethoxy.

Preferred are enantiomerically pure, solvent-free, crystalline forms of compounds of formula 1-base, wherein R$^1$ and R$^2$ which may be identical or different, preferably identical, denote ethyl or propyl, or together denote —CH$_2$—CH$_2$—, —CH$_2$—CH$_2$—CH$_2$— or —CH$_2$-CH$_2$-CH$_2$—CH$_2$—

R$^3$ denotes hydrogen, fluorine, OH, methyl or methoxy, preferably hydrogen.

Particularly preferred are enantiomerically pure, solvent-free, crystalline forms of compounds of formula 1.7-base—N-(5-{2-[1,1-dimethyl-3-(2-oxo-4,4-dipropyl-4H-benzo[d][1,3]oxazin-1-yl)-propylamino]-1-hydroxy-ethyl}-2-hydroxy-phenyl)-methanesulphonamide 1.8-base—N-[5-(2-{1,1-dimethyl-3-[spiro(cyclohexane-1, 4'-2H-3',1'-benzoxazin)-2'-oxo-1-yl]-propylamino}-1-hydroxy-ethyl)-2-hydroxy-phenyl]-methanesulphonamide 1.9-base—N-[5-(2-{1,1-dimethyl-3-[spiro(cyclopropyl-1, 4'-2H-3',1'-benzoxazin)-2'-oxo-1-yl]-propylamino}-1-hydroxy-ethyl)-2-hydroxy-phenyl]-methanesulphonamide 1.10-base—N-(5-{2-[3-(4,4-diethyl-2-oxo-4H-benzo[d][1, 3]oxazin-1-yl)-1,1-dimethyl-propylamino]-1-hydroxy-ethyl}-2-hydroxy-phenyl)-methanesulphonamide 1.11-base—N-(5-{2-[3-(4,4-diethyl-6-fluoro-2-oxo-4H-benzo[d][1,3]oxazin-1-yl)-1,1-dimethyl-propylamino]-1-hydroxy-ethyl}-2-hydroxy-phenyl)-methanesulphonamide 1.12-base—N-(5-{2-[3-(4,4-diethyl-7-fluoro-2-oxo-4H-benzo[d][1,3]oxazin-1-yl)-1,1-dimethyl-propylamino]-1-hydroxy-ethyl}-2-hydroxy-phenyl)-methanesulphonamide 1.13-base—N-(5-{2-[3-(4,4-diethyl-8-methoxy-2-oxo-4H-benzo[d][1,3]oxazin-1-yl)-1,1-dimethyl-propylamino]-1-hydroxy-ethyl}-2-hydroxy-phenyl)-methanesulphonamide 1.14-base—N-(5-{2-[3-(4,4-diethyl-6-methoxy-2-oxo-4H-benzo[d][1,3]oxazin-1-yl)-1,1-dimethyl-propylamino]-1-hydroxy-ethyl}-2-hydroxy-phenyl)-methanesulphonamide

TERMS AND DEFINITIONS USED

By the term "$C_{1-4}$-alkyl" (including those which are part of other groups) are meant branched and unbranched alkyl groups with 1 to 4 carbon atoms. Examples include: methyl, ethyl, n-propyl, iso-propyl, n-butyl, iso-butyl, sec-butyl or tert-butyl. The abbreviations Me, Et, n-Pr, i-Pr, n-Bu, i-Bu, t-Bu, etc. may optionally also be used for the above-mentioned groups. Unless stated otherwise, the definitions propyl and butyl include all the possible isomeric forms of the groups in question. Thus, for example, propyl includes n-propyl and iso-propyl, butyl includes iso-butyl, sec-butyl and tert-butyl etc.

By the term "$C_{1-6}$-alkylene" (including those which are part of other groups) are meant branched and unbranched alkylene groups with 1 to 6 carbon atoms and by the term "$C_{1-4}$-alkylene" are meant branched and unbranched alkylene groups with 1 to 4 carbon atoms. Alkylene groups with 1 to 4 carbon atoms are preferred. Examples include: methylene, ethylene, propylene, 1-methylethylene, butylene, 1-methylpropylene, 1,1-dimethylethylene, 1,2-dimethylethylene, pentylene, 1,1-dimethylpropylene, 2,2-dimethylpropylene, 1,2-dimethylpropylene, 1.3-dimethylpropylene or hexylene. Unless stated otherwise, the definitions propylene, butylene, pentylene and hexylene include all the possible isomeric forms of the groups in question with the same number of carbons. Thus, for example, propyl also includes 1-methylethylene and butylene includes 1-methylpropylene, 1,1-dimethylethylene, 1,2-dimethylethylene.

Halogen within the scope of the present invention represents fluorine, chlorine, bromine or iodine. Unless stated to the contrary, fluorine, chlorine and bromine are regarded as preferred halogens.

The term enantiomerically pure describes, within the scope of the present invention, compounds of formula 1 which are present in an enantiomeric purity of at least 85% ee, preferably at least 90% ee, particularly preferably >95% ee. The term ee (enantiomeric excess) is known in the art and describes the optical purity of chiral compounds.

The term solvent-free within the scope of the present invention describes compounds of formula 1-base in crystalline form, wherein no solvents are incorporated in the crystalline union in a defined stoichiometric ratio in lattice locations of the crystal.

INDICATIONS

The compounds of formula 1 according to the invention are characterised by their versatility of use in the therapeutic field. Particular mention should be made according to the invention of the possible applications for which the compounds according to the invention of formula 1 are preferably used on account of their pharmaceutical activity as betamimetics.

In another aspect the present invention correspondingly relates to the above-mentioned enantiomerically pure compounds of formula 1 as pharmaceutical compositions. The present invention further relates to the use of the above-mentioned compounds of general formula 1 for preparing a pharmaceutical composition for the treatment of respiratory complaints. The present invention preferably relates to the use of the above-mentioned compounds of general formula 1 for preparing a pharmaceutical composition for the treatment of respiratory complaints, which are selected from among obstructive pulmonary diseases of various origins, pulmonary emphysema of various origins, restrictive pulmonary diseases, interstitial pulmonary diseases, cystic fibrosis, bronchitis of various origins, bronchiectasis, ARDS (adult respiratory distress syndrome) and all forms of pulmonary oedema.

Preferably the compounds of general formula 1 are used to prepare a pharmaceutical composition for the treatment of obstructive pulmonary diseases selected from among COPD (chronic obstructive pulmonary disease), bronchial asthma, paediatric asthma, severe asthma, acute asthma attacks and chronic bronchitis, while it is particularly preferable according to the invention to use them for preparing a pharmaceutical composition for the treatment of bronchial asthma.

Preferably also, the compounds of formula 1 are used to prepare a pharmaceutical composition for the treatment of pulmonary emphysema which has its origins in COPD (chronic obstructive pulmonary disease) or α1-proteinase inhibitor deficiency.

Preferably also, the compounds of formula 1 are used to prepare a pharmaceutical composition for the treatment of restrictive pulmonary diseases selected from among allergic alveolitis, restrictive pulmonary diseases triggered by work-related noxious substances, such as asbestosis or silicosis, and restriction caused by lung tumours, such as for example lymphangiosis carcinomatosa, bronchoalveolar carcinoma and lymphomas.

Preferably also, the compounds of formula 1 are used to prepare a pharmaceutical composition for the treatment of interstitial pulmonary diseases selected from among pneumonia caused by infections, such as for example infection by viruses, bacteria, fungi, protozoa, helminths or other pathogens, pneumonitis caused by various factors, such as for example aspiration and left heart insufficiency, radiation-induced pneumonitis or fibrosis, collagenoses, such as for example lupus erythematodes, systemic sclerodermy or sarcoidosis, granulomatoses, such as for example Boeck's disease, idiopathic interstitial pneumonia or idiopathic pulmonary fibrosis (IPF).

Preferably also, the compounds of general formula 1 are used to prepare a pharmaceutical composition for the treatment of cystic fibrosis or mucoviscidosis.

Preferably also, the compounds of general formula 1 are used to prepare a pharmaceutical composition for the treatment of bronchitis, such as for example bronchitis caused by bacterial or viral infection, allergic bronchitis and toxic bronchitis.

Preferably also, the compounds of general formula 1 are used to prepare a pharmaceutical composition for the treatment of bronchiectasis.

Preferably also, the compounds of general formula 1 are used to prepare a pharmaceutical composition for the treatment of ARDS (adult respiratory distress syndrome).

Preferably also, the compounds of general formula 1 are used to prepare a pharmaceutical composition for the treatment of pulmonary oedema, for example toxic pulmonary oedema after aspiration or inhalation of toxic substances and foreign substances.

Particularly preferably, the present invention relates to the use of the compounds of formula 1 for preparing a pharmaceutical composition for the treatment of asthma or COPD. Also of particular importance is the above-mentioned use of compounds of formula 1 for preparing a pharmaceutical composition for once-a-day treatment of inflammatory and obstructive respiratory complaints, particularly for the once-a-day treatment of asthma or COPD.

The present invention also relates to a process for the treatment of the above-mentioned diseases, characterised in that one or more of the above-mentioned compounds of general formula 1 are administered in therapeutically effective amounts. The present invention further relates to processes for the treatment of asthma or COPD, characterised in that one or more of the above-mentioned compounds of general formula 1 are administered once a day in therapeutically effective amounts.

The compounds according to the invention may be prepared by the method shown diagrammatically in Scheme 1.

EXAMPLES

Example 1

N-(5-{2-[1,1-dimethyl-3-(4-methyl-2-oxo-4H-benzo[d][1,3]oxazin-1-yl)-propylamino]-1-hydroxy-ethyl}-2-hydroxy-phenyl)-methanesulphonamide

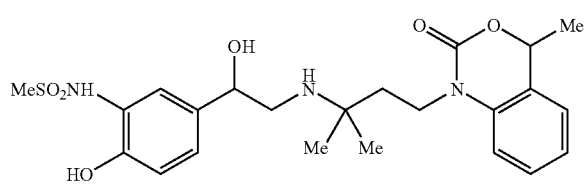

The compound is known from EP 43940. The individual diastereomers of this embodiment may be obtained by common methods known in the art.

Example 2

N-(5-{2-[1,1-dimethyl-3-(2-oxo-4H-benzo[d][1,3]oxazin-1-yl)-propylamino]-1-hydroxy-ethyl}-2-hydroxy-phenyl)-methanesulphonamide

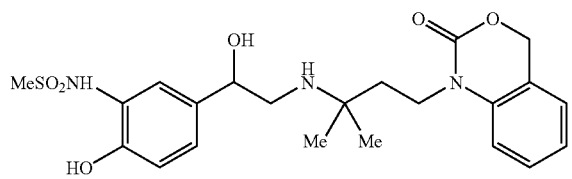

The compound is known from EP 43940. The (R)- and (S)-enantiomers of this embodiment may be obtained by common methods known in the art.

Example 3

N-(5-{2-[3-(4-ethyl-2-oxo-4H-benzo[d][1,3]oxazin-1-yl)-1,1-dimethyl-propylamino]-1-hydroxy-ethyl}-2-hydroxy-phenyl)-methanesulphonamide

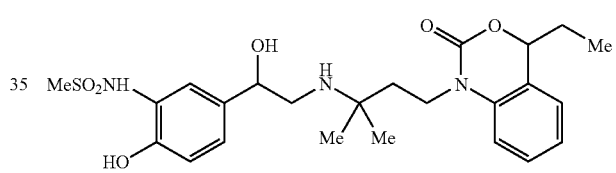

The compound is known from EP 43940. The individual diastereomers of this embodiment may be obtained by common methods known in the art.

Example 4

N-(5-{2-[3-(4,4-dimethyl-2-oxo-4H-benzo[d][1,3]oxazin-1-yl)-1,1-dimethyl-propylamino]-1-hydroxy-ethyl}-2-hydroxy-phenyl)-methanesulphonamide

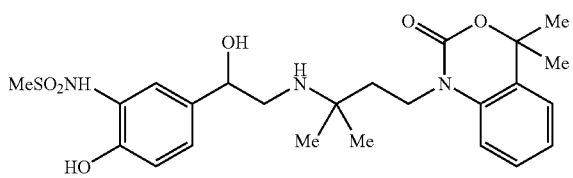

The compound is known from EP 43940. The (R)- and (S)-enantiomers of this embodiment may be obtained by common methods known in the art.

Example 5

N-(2-hydroxy-5-{1-hydroxy-2-[3-(6-hydroxy-4,4-dimethyl-2-oxo-4H-benzo[d][1,3]oxazin-1-yl)-1,1-dimethyl-propylamino]-ethyl}-phenyl)-methane-sulphonamide

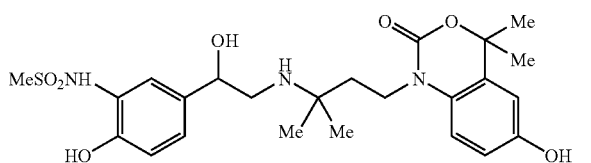

The compound is known from EP 43940. The (R)- and (S)-enantiomers of this embodiment may be obtained by common methods known in the art.

Example 6

N-(2-hydroxy-5-{1-hydroxy-2-[3-(6-methoxy-4,4-dimethyl-2-oxo-4H-benzo[d][1,3]oxazin-1-yl)-1,1-dimethyl-propylamino]-ethyl}-phenyl)-methane-sulphonamide

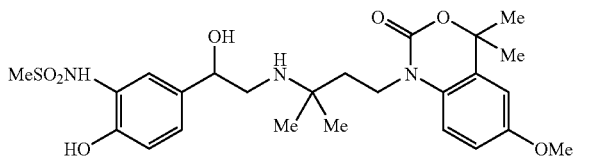

The compound is known from EP 43940. The (R)- and (S)-enantiomers of this embodiment may be obtained by common methods known in the art.

The examples of synthesis described below serve to illustrate new compounds according to the invention in more detail. However, they are intended only as examples of procedures to illustrate the invention without restricting it to the subject matter described in an exemplifying capacity hereinafter.

HPLC method (method A): Symmetry C18 (Waters): 3.5 µm; 4.6×150 mm; column temperature: 20° C.; gradient: acetonitrile/phosphate buffer (pH 7) 20:80→80:20 in 30 minutes; flow: 1.0 mL/min; detection at 220 and 254 nm.

Synthesis of Intermediate Products 1-8

Intermediate Product 1: 1-(3-amino-3-methyl-butyl)-4,4-dipropyl-1,4-dihydro-benzo[d][1,3]oxazin-2-one

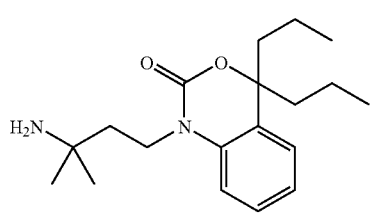

a) 4-(2-amino-phenyl)-heptan-4-ol: 90 mL (180.0 mmol) propylmagnesium chloride (2 M in ether) are added dropwise to a solution of 7.00 mL (54.0 mmol) methyl anthranilate in abs. THF (70 mL) at 0° C. within 30 minutes. The mixture is stirred for one hour at ambient temperature and then combined with 100 mL of 3 molar aqueous ammonium chloride solution and ethyl acetate. The phases are separated and the aqueous phase is exhaustively extracted with ethyl acetate. The combined organic phases are washed with potassium hydrogen carbonate solution and saturated sodium chloride solution and dried on sodium sulphate. The crude product is used in the next reaction step without further purification.

Yield: 6.70 g (60%).

b) tert-butyl{3-[2-(1-hydroxy-1-propyl-butyl)-phenylamino]-1,1-dimethyl-propyl}-carbamate: 1.40 g (22.27 mmol) sodium cyanoborohydride are added to a solution of 3.10 g (14.05 mmol) 4-(2-amino-phenyl)-heptan-4-ol and 3.60 g (17.88 mmol) tert-butyl(1,1-dimethyl-3-oxo-propyl)-carbamate in methanol (40 mL) and acetic acid (6 mL). The mixture is stirred for 16 hours at ambient temperature, diluted with ethyl acetate, washed with 0.5 molar potassium hydrogen sulphate solution and saturated sodium chloride solution, dried on sodium sulphate and evaporated down in vacuo. The crude product is used in the next reaction step without further purification. Yield: 6.00 g (quantitative yield).

c) tert-butyl[1,1-dimethyl-3-(2-oxo-4,4-dipropyl-4H-benzo[d][1,3]oxazin-1-yl)-propyl]-carbamate: 8.85 mL (16.81 mmol) phosgene solution (20 wt. % in toluene) are slowly added dropwise at 0° C. to a solution of 6.00 g (15.28 mmol) tert-butyl{3-[2-(1-hydroxy-1-propyl-butyl)-phenylamino]-1,1-dimethyl-propyl}-carbamate and 5.32 mL (38.21 mmol) triethylamine in abs. THF (80 mL). The mixture is stirred for 2 hours at ambient temperature, diluted with ethyl acetate, combined with ice and made basic with saturated aqueous ammonia solution. The aqueous phase is exhaustively extracted with ethyl acetate and the combined organic phases are washed with saturated sodium chloride solution, dried on sodium sulphate and evaporated down in vacuo. After column chromatography (silica gel, cyclohexane/ethyl acetate=6:1) the product is obtained. Yield: 4.57 g (71%).

d) 1-(3-amino-3-methyl-butyl)-4,4-dipropyl-1,4-dihydro-benzo[d][1,3]oxazin-2-one: A solution of 4.20 g (10.03 mmol) tert-butyl[1,1-dimethyl-3-(2-oxo-4,4-dipropyl-4H-benzo[d][1,3]oxazin-1-yl)-propyl]-carbamate in 35 mL formic acid is stirred for 24 hours at ambient temperature and then poured onto ice. The aqueous phase is made basic with saturated aqueous ammonia solution and exhaustively extracted with ethyl acetate. The combined organic extracts are washed with sodium chloride solution, dried on sodium sulphate and evaporated down in vacuo. The residue is taken up in ethyl acetate (50 mL) and combined with 4 mL hydrochloric acid in ethyl acetate (saturated). The solution is evaporated down and twice mixed with a little ethanol and evaporated down in vacuo. Trituration of the residue with diisopropylether yields the product as the hygroscopic hydrochloride salt.

Yield: 2.60 g (73%).

Intermediate Product 2: 1-(3-amino-3-methyl-butyl)-4,4-diethyl-7-fluoro-1,4-dihydro-benzo[d][1,3]oxazin-2-one

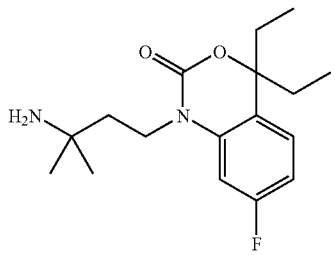

a) 3-(2-amino-4-fluoro-phenyl)-pentan-3-ol: The product is obtained analogously to intermediate product 1a by reacting methyl 2-amino-4-fluoro-benzoate and ethylmagnesium bromide in dichloromethane at −78° C. with heating to ambient temperature. Yield: 4.1 g (99%).

b) tert-butyl{3-[2-(1-ethyl-1-hydroxy-propyl)-5-fluoro-phenylamino]-1,1-dimethyl-propyl}-carbamate: The product is obtained analogously to intermediate product 1b starting from 3-(2-amino-4-fluoro-phenyl)-pentan-3-ol and tert-butyl(1,1-dimethyl-3-oxo-propyl)-carbamate. The crude product is purified by column chromatography (silica gel, dichloromethane/methanol=100:0→98:2).

Yield: 7.70 g (99%).

c) tert-butyl[3-(4,4-diethyl-7-fluoro-2-oxo-4H-benzo[d][1,3]oxazin-1-yl)-1,1-dimethyl-propyl]-carbamate: The product is obtained analogously to intermediate product 1c starting from tert-butyl{3-[2-(1-ethyl-1-hydroxy-propyl)-5-fluoro-phenylamino]-1,1-dimethyl-propyl}-carbamate. Yield: 4.20 g (51%).

d) 1-(3-amino-3-methyl-butyl)-4,4-diethyl-7-fluoro-1,4-dihydro-benzo[d][1,3]oxazin-2-one: The product is prepared analogously to intermediate product 1d starting from tert-butyl[3-(4,4-diethyl-7-fluoro-2-oxo-4H-benzo[d][1,3]oxazin-1-yl)-1,1-dimethyl-propyl]-carbamate as the free base.

Yield: 2.90 g (96%); ESI-MS: [M+H]$^+$=309.

Intermediate Product 3: 1-(3-amino-3-methyl-butyl)-spiro(cyclopropyl-1,4'-2H-3',1'-benzoxazin)-2'-one

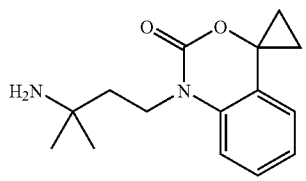

a) 1-(2-dibenzylamino-phenyl)-cyclopropanol: 2.45 mL (8.4 mmol) titanium tetraisopropoxide are slowly added dropwise at ambient temperature to a solution of 18.5 g (55.8 mmol) methyl 2-dibenzylamino-benzoate in 150 mL THF. After one hour's stirring 40.9 mL (122.7 mmol) ethylmagnesium bromide (3 M in diethyl ether) are added. The mixture is stirred for one hour, another 4 mL of 3 molar ethylmagnesium bromide solution are added and the mixture is stirred for 2 hours. The reaction mixture is combined with saturated ammonium chloride solution and extracted with ethyl acetate. The aqueous phase is combined with 1 molar hydrochloric acid until a clear solution is obtained and extracted with ethyl acetate. The combined organic phases are washed with sodium hydrogen carbonate solution and sodium chloride solution, dried on sodium sulphate and evaporated down. The residue is purified by chromatography (hexane/ethyl acetate=20:1). Yield: 10.0 g (54%).

b) 1-(2-amino-phenyl)-cyclopropanol: 9.90 g (30.1 mmol) 1-(2-dibenzylamino-phenyl)-cyclopropanol are dissolved in 70 mL methanol and hydrogenated in the presence of 1 g palladium on charcoal (10%) at 3 bar hydrogen pressure. The catalyst is removed by suction filtering, the filtrate is evaporated down and the residue is purified by chromatography (silica gel; cyclohexane/ethyl acetate=5:1). Yield: 1.80 g (40%).

c) tert-butyl{3-[2-(1-hydroxy-cyclopropyl)-phenylamino]-1,1-dimethyl-propyl}-carbamate: Prepared analogously to the method described for intermediate product 1b from 1.77 g (11.86 mmol) 1-(2-amino-phenyl)-cyclopropanol and 3.15 g (15.66 mmol) tert-butyl(1,1-dimethyl-3-oxo-propyl)-carbamate. The crude product obtained is purified by column chromatography (silica gel, cyclohexane/ethyl acetate 4:1).

Yield: 2.60 g.

d) tert-butyl{1,1-dimethyl-3-[spiro(cyclopropyl-1,4'-2H-3',1'-benzoxazin)-2'-oxo-1-yl]-propyl}-carbamate: The product is obtained analogously to intermediate product 1c starting from 2.60 g (7.74 mmol) tert-butyl{3-[2-(1-hydroxy-cyclopropyl)-phenylamino]-1,1-dimethyl-propyl}-carbamate. A difference here is that there is no purification by column chromatography. Yield: 2.60 g.

e) 1-(3-amino-3-methyl-butyl)-spiro(cyclopropyl-1,4'-2H-3',1'-benzoxazin)-2'-one: Obtained analogously to the method described for Intermediate 1d by reacting 3.10 g (8.60 mmol) tert-butyl{1,1-dimethyl-3-[spiro(cyclopropyl-1,4'-2H-3',1'-benzoxazin)-2'-oxo-1-yl]-propyl}-carbamate and 30 mL formic acid. Yellow oil.

Yield: 2.10 g (94%).

Intermediate Product 4: 1-(3-amino-3-methyl-butyl)-4,4-diethyl-1,4-dihydro-benzo[d][1,3]oxazin-2-one

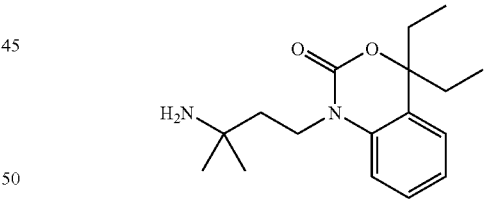

a) 3-(2-amino-phenyl)-pentan-3-ol: 100 mL of a 3 molar ethylmagnesium bromide solution in diethyl ether are added dropwise at −40° C. to a solution of 7.77 mL (60 mmol) 2-amino-methylbenzoic acid in 130 mL THF. The mixture is stirred overnight with heating to ambient temperature, combined with saturated ammonium chloride solution, acidified with 1 molar hydrochloric acid and extracted with ethyl acetate. The combined organic phases are extracted with water, dried on sodium sulphate and evaporated down. Oil, which crystallises out and is further reacted directly. Yield: 10.9 g; mass spectroscopy: [M+H]$^+$=180.

b) tert-butyl{3-[2-(1-ethyl-1-hydroxy-propyl)-phenylamino]-1,1-dimethyl-propyl}-carbamate: 3.16 g (47.7 mmol) sodium cyanoborohydride are added at ambient temperature to 5.70 g (31.8 mmol) 3-(2-amino-phenyl)-pentan- 3-ol and 2.63 mL (47.7 mmol) acetic acid in 18 mL methanol. Then a solution of 7.04 g (35 mmol) tert-butyl(1,1-dimethyl-3-oxo-propyl)-carbamate in 18 mL methanol is slowly added dropwise. After the addition has ended the mixture is stirred for four hours, combined with 1 molar hydrochloric acid (development of gas) and then made basic with aqueous ammonia solution. It is extracted with ethyl acetate and the combined organic phases are washed with sodium chloride solution, dried on sodium sulphate and freed from the solvent. The residue is purified by column chromatography (silica gel, dichloromethane/methanol gradient with 0.1% ammonia). Yield: 4.25 g (37%); mass spectroscopy: [M+H]$^+$=365.

c) tert-butyl[3-(4,4-diethyl-2-oxo-4H-benzo[d][1,3]oxazin-1-yl)-1,1-dimethyl-propyl]-carbamate: 2.91 g (9.6 mmol) triphosgene are added at 0 to 5° C. to a solution of 3.50 g (9.6 mmol) tert-butyl{3-[2-(1-ethyl-1-hydroxy-propyl)-phenylamino]-1,1-dimethyl-propyl}-carbamate and 3.37 mL (24 mmol) triethylamine in 35 mL THF. The mixture is left overnight at ambient temperature with stirring and the precipitate formed is suction filtered. The filtrate is evaporated down and the crude product remaining is further reacted directly.

Yield: 3.33 g; mass spectroscopy: [M+H]$^+$=391.

d) 1-(3-amino-3-methyl-butyl)-4,4-diethyl-1,4-dihydro-benzo[d][1,3]oxazin-2-one: 25 mL trifluoroacetic acid are added dropwise, while being cooled with the ice bath, to a solution of 3.20 g tert-butyl[3-(4,4-diethyl-2-oxo-4H-benzo[d][1,3]oxazin-1-yl)-1,1-dimethyl-propyl]-carbamate (approx. 75%) in 25 mL dichloromethane. The mixture is stirred for 2 hours at ambient temperature, the solvents are distilled off and the acid residues are eliminated by repeated codistillation with toluene. To liberate the free base the residue is combined with 1 molar sodium hydroxide solution and extracted with ethyl acetate. The organic phases are dried on sodium sulphate and evaporated down. The free base is dissolved in 8 mL methanol and combined with ethereal hydrochloric acid. It is stirred overnight and the precipitate formed is suction filtered and washed with diethyl ether. Yield: 2.15 g (hydrochloride); mass spectroscopy: [M+H]$^+$=291.

Intermediate Product 5: 1-(3-amino-3-methyl-butyl)-spiro(cyclohexane-1,4'-2H-3',1'-benzoxazin)-2'-one

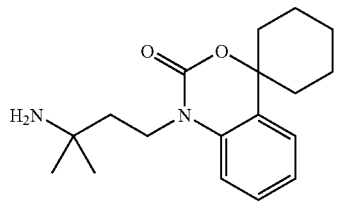

a) 1-(2-nitro-phenyl)-cyclohexanol: 40.16 mL (80.32 mmol) phenylmagnesium chloride (2 M in THF) are added dropwise at −50° C. under nitrogen to a solution of 20.0 g (80.32 mmol) 2-nitro-iodobenzene in 150 mL THF. After 15 minutes stirring 9.98 mL (96.30 mmol) cyclohexanone are quickly added. The reaction mixture is heated to ambient temperature, stirred for two hours and combined with ammonium chloride solution. The aqueous phase is separated off and exhaustively extracted with ethyl acetate. The combined organic phases are washed with sodium chloride solution, dried on sodium sulphate and evaporated down. Column chromatography (silica gel, hexane/ethyl acetate=20:1) yields the product. Yield: 5.20 g (29%); R$_f$=0.26 (silica gel, hexane/ethyl acetate=10:1); ESI-MS: [M+H—H$_2$O]$^+$=204.

b) 1-(2-amino-phenyl)-cyclohexanol: 5.20 g (16.45 mmol) 1-(2-nitro-phenyl)-cyclohexanol in 70 mL ethanol are hydrogenated for 4 hours in the presence of Raney nickel at ambient temperature and 3 bar hydrogen pressure. The catalyst is filtered off through Celite and the filtrate is evaporated down in vacuo. The residue is precipitated from hexane. Yield: 1.53 g (49%); R$_f$=0.38 (silica gel, hexane/ethyl acetate=4:1); ESI-MS: [M+H—H$_2$O]$^+$=174.

c) tert-butyl{3-[2-(1-hydroxy-cyclohexyl)-phenylamino]-1,1-dimethyl-propyl}-carbamate: The compound is obtained analogously to intermediate product 1b from 1-(2-amino-phenyl)-cyclohexanol and tert-butyl(1,1-dimethyl-3-oxo-propyl)-carbamate. Column chromatography (silica gel, hexane/ethyl acetate=7:1) yields the product. Yield: 2.65 g (66%); R$_f$=0.50 (silica gel, hexane/ethyl acetate=4:1).

d) tert-butyl{1,1-dimethyl-3-[spiro(cyclohexane-1,4'-2H-3'1'-benzoxazin)-2'-oxo-1-yl]-propyl}-carbamate: Prepared analogously to intermediate product 1c from tert-butyl{3-[2-(1-hydroxy-cyclohexyl)-phenylamino]-1,1-dimethyl-propyl}-carbamate. Yield: 2.60 g (92%); R$_f$=0.38 (silica gel, hexane/ethyl acetate 4:1).

e) 1-(3-amino-3-methyl-butyl)-spiro(cyclohexane-1,4'-2H-3',1'-benzoxazin)-2'-one: Prepared analogously to intermediate product 1d from tert-butyl[1,1-dimethyl-3-(spiro(cyclohexane-1,4'-2H-3',1'-benzoxazin)-2'-oxo-1-yl)-propyl]-carbamate.

Yield: 1.80 g (92%); R$_f$=0.10 (silica gel, dichloromethane/methanol/ammonia=95:5:0.5); ESI-MS: [M+H]$^+$=303.

Intermediate Product 6: 1-(3-amino-3-methyl-butyl)-4,4-diethyl-8-methoxy-1,4-dihydro-benzo[d][1,3]oxazin-2-one

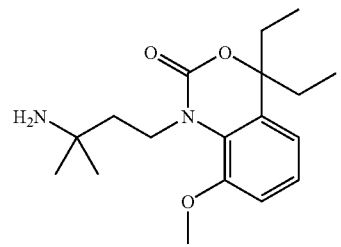

a) 3-(2-amino-3-methoxy-phenyl)-pentan-3-ol: The product is obtained analogously to intermediate product 1a by reacting methyl 2-amino-3-methoxy-benzoate and ethylmagnesium bromide in dichloromethane at −78° C.→RT. Yield: 5.20 g (92%); HPLC-MS: R$_t$=12.85 min. (method A); ESI-MS: [M+H]$^+$=210.

b) tert-butyl{3-[2-(1-ethyl-1-hydroxy-propyl)-6-methoxy-phenylamino]-1,1-dimethyl-propyl}-carbamate: The product is obtained analogously to intermediate product 1b starting from 3-(2-amino-3-methoxy-phenyl)-pentan-3-ol and tert-butyl(1,1-dimethyl-3-oxo-propyl)-carbamate. The crude product is purified by column chromatography (silica gel, cyclohexane/ethyl acetate=4:1). Yield: 4.60 g (47%).

c) tert-butyl[3-(4,4-diethyl-8-methoxy-2-oxo-4H-benzo[d][1,3]oxazin-1-yl)-1,1-dimethyl-propyl]-carbamate: The product is obtained analogously to intermediate product 1c starting from tert-butyl{3-[2-(1-ethyl-1-hydroxy-propyl)-6-methoxy-phenylamino]-1,1-dimethyl-propyl}-carbamate. Yield: 4.60 g (94%).

d) 1-(3-amino-3-methyl-butyl)-4,4-diethyl-8-methoxy-1,4-dihydro-benzo[d][1,3]oxazin-2-one: The product is obtained analogously to intermediate product 1d starting from tert-butyl[3-(4,4-diethyl-8-methoxy-2-oxo-4H-benzo[d][1,3]oxazin-1-yl)-1,1-dimethyl-propyl]-carbamate as a free base.

Yield: 3.00 g (93%); ESI-MS: [M+H]$^+$=321.

Intermediate Product 7: 1-(3-amino-3-methyl-butyl)-4,4-diethyl-6-fluoro-1,4-dihydro-benzo[d][1,3]oxazin-2-one

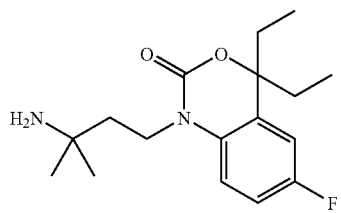

a) 3-(2-amino-5-fluoro-phenyl)-pentan-3-ol: Prepared analogously to intermediate product 1a from methyl 2-amino-5-fluoro-benzoate and ethylmagnesium bromide. The product obtained is purified by chromatography (silica gel, cyclohexane/ethyl acetate=8:1). Yield: 6.00 g (74%).

b) tert-butyl{3-[2-(1-ethyl-1-hydroxy-propyl)-4-fluoro-phenylamino]-1,1-dimethyl-propyl}-carbamate: The product is obtained analogously to intermediate product 1b starting from 3-(2-amino-5-fluoro-phenyl)-pentan-3-ol and tert-butyl(1,1-dimethyl-3-oxo-propyl)-carbamate. The crude product is purified by column chromatography (silica gel, hexane/ethyl acetate=6:1→2:1). Yield: 4.50 g (41%).

c) tert-butyl[3-(4,4-diethyl-6-fluoro-2-oxo-4H-benzo[d][1,3]oxazin-1-yl)-1,1-dimethyl-propyl]-carbamate: Prepared analogously to intermediate product 1c from tert-butyl{3-[2-(1-ethyl-1-hydroxy-propyl)-4-fluoro-phenylamino]-1,1-dimethyl-propyl}-carbamate. A difference here is that there is no purification by column chromatography. Yield: 4.8 g.

d) 1-(3-amino-3-methyl-butyl)-4,4-diethyl-6-fluoro-1,4-dihydro-benzo[d][1,3]oxazin-2-one: The target compound is prepared as a free base analogously to intermediate product 1d from tert-butyl[3-(4,4-diethyl-6-fluoro-2-oxo-4H-benzo[d][1,3]oxazin-1-yl)-1,1-dimethyl-propyl]-carbamate. Yield: 3.00 g (99%).

Intermediate Product 8: 1-(3-amino-3-methyl-butyl)-4,4-diethyl-6-methoxy-1,4-dihydro-benzo[d][1,3]oxazin-2-one

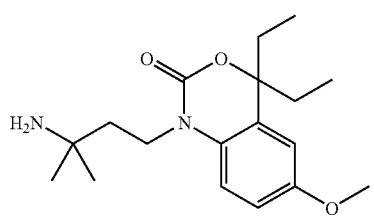

a) 3-(2-amino-5-methoxy-phenyl)-pentan-3-ol: the product is obtained by reacting 4.00 g (22 mmol) methyl 2-amino-5-methoxy-benzoate with 5 equivalents ethylmagnesium bromide in dichloromethane at −78° C.->RT. Yield: 4.47 g (97%).

b) tert-butyl{3-[2-(1-ethyl-1-hydroxy-propyl)-4-methoxy-phenylamino]-1,1-dimethyl-propyl}-carbamate: Prepared analogously to intermediate product 1b from 4.45 g (21 mmol) 3-(2-amino-5-methoxy-phenyl)-pentan-3-ol and 5.66 g (28 mmol) tert-butyl(1,1-dimethyl-3-oxo-propyl)-carbamate. Yield: 6.00 g (72%).

c) tert-butyl[3-(4,4-diethyl-6-methoxy-2-oxo-4H-benzo[d][1,3]oxazin-1-yl)-1,1 dimethyl-propyl]-carbamate: The product is prepared analogously to intermediate product 1c from 6.00 g (15.2 mmol) tert-butyl{3-[2-(1-ethyl-1-hydroxy-propyl)-4-methoxy-phenylamino]-1,1-dimethyl-propyl}-carbamate. Yield: 3.10 g (48%).

d) 1-(3-amino-3-methyl-butyl)-4,4-diethyl-6-methoxy-1,4-dihydro-benzo[d][1,3]oxazin-2-one: Prepared analogously to intermediate product 1d from 3.10 g (8.5 mmol) tert-butyl [3-(4,4-diethyl-6-methoxy-2-oxo-4H-benzo[d][1,3]oxazin-1-yl)-1,1-dimethyl-propyl]-carbamate. The product is isolated as the free base and not converted into a hydrochloride salt. Yield: 2.20 g (98%).

Example 7

N-(5-{2-[1,1-dimethyl-3-(2-oxo-4,4-dipropyl-4H-benzo[d][1,3]oxazin-1-yl)-propylamino]-1-hydroxy-ethyl}-2-hydroxy-phenyl)-methanesulphonamide

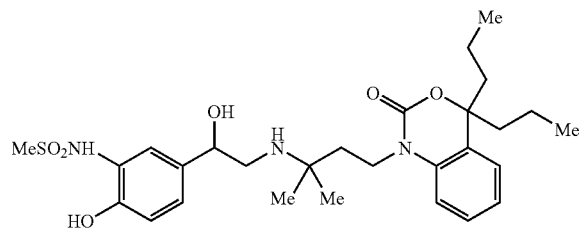

a) N-(2-benzyloxy-5-{2-[1,1-dimethyl-3-(2-oxo-4,4-dipropyl-4H-benzo[d][1,3]oxazin-1-yl)-propylamino]-1-hydroxy-ethyl}-phenyl)-methanesulphonamide: 86 µl (0.619 mmol) triethylamine are added at ambient temperature under a nitrogen atmosphere to a solution of 200 mg (0.564 mmol) 1-(3-amino-3-methyl-butyl)-4,4-dipropyl-1,4-dihydro-benzo[d][1,3]oxazin-2-one hydrochloride in 5 mL THF. The mixture is stirred for 30 minutes, 218 mg (0.575 mmol) N-[2-benzyloxy-5-(2-ethoxy-2-hydroxy-acetyl)-phenyl]-methanesulphonamide are added and the mixture is stirred for a further 2 hours at ambient temperature. The mixture is cooled to 10° C., combined with 51 mg (2.34 mmol) lithium borohydride, heated to ambient temperature and stirred for one hour. It is cooled to 10° C. again and diluted with 15 mL water and 20 mL dichloromethane. The aqueous phase is separated off and extracted with dichloromethane. The combined organic phases are dried on sodium sulphate and evaporated down in vacuo. The residue is dissolved in 8 mL ethyl acetate and acidified to pH 2 by the addition of saturated hydrochloric acid in ethyl acetate. The precipitate formed is filtered off, washed with ethyl acetate and evaporated down. Yield: 260 mg (67%, hydrochloride), HPLC: $R_t$=19.8 minutes (method A).

b) N-(5-{2-[1,1-dimethyl-3-(2-oxo-4,4-dipropyl-4H-benzo[d][1,3]oxazin-1-yl)-propylamino]-1-hydroxy-ethyl}-2-hydroxy-phenyl)-methanesulphonamide: 260 mg (0.386 mmol) N-(2-benzyloxy-5-{2-[1,1-dimethyl-3-(2-oxo-4,4-dipropyl-4H-benzo[d][1,3]oxazin-1-yl)-propylamino]-1-hydroxy-ethyl}-phenyl)-methanesulphonamide hydrochloride in 8 mL methanol are hydrogenated in the presence of 26 mg palladium on charcoal (10%) at ambient temperature. The catalyst is filtered off through Celite and washed with methanol. The filtrate is evaporated down in vacuo and the residue is stirred into diethyl ether.

Yield: 120 mg (53%, hydrochloride); mass spectroscopy: [M+H]$^+$=548; HPLC: R$_f$=14.7 minutes (method A).

The (R)- and (S)-enantiomers of this embodiment may be obtained by common methods known in the art. The (R)-enantiomer of this embodiment is of particular importance according to the invention.

Example 8

N-[5-(2-{1,1-dimethyl-3-[spiro(cyclohexane-1,4'-2H-3',1'-benzoxazin)-2'-oxo-1-yl]-propylamino}-1-hydroxy-ethyl)-2-hydroxy-phenyl]-methanesulphonamide

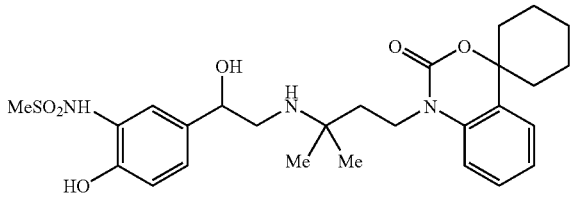

a) N-[2-benzyloxy-5-(2-{3-[spiro(cyclohexane-1,4'-2H-3',1'-benzoxazin)-2'-oxo-1-yl]-1,1-dimethyl-propylamino}-1-hydroxy-ethyl]-phenyl]-methanesulphonamide: Prepared analogously to the process described for Example 7a from 250 mg (0.66 mmol) N-[2-benzyloxy-5-(2-ethoxy-2-hydroxy-acetyl)-phenyl]-methanesulphonamide and 200 mg (0.66 mmol) 1-(3-amino-3-methyl-butyl)-spiro(cyclohexane-1,4'-2H-3',1'-benzoxazin)-2'-one. A difference here is that the product obtained as the hydrochloride is also purified by chromatography (silica gel, dichloromethane/methanol=50:1).

Yield: 190 mg (46%), HPLC: R$_f$=17.8 minutes (method A).

b) N-[5-(2-{1,1-dimethyl-3-[spiro(cyclohexane-1,4'-2H-3',1'-benzoxazin)-2'-oxo-1-yl]-propylamino}-1-hydroxy-ethyl)-2-hydroxy-phenyl]-methanesulphonamide: 190 mg (0.31 mmol) N-[2-benzyloxy-5-(2-{3-[spiro(cyclohexane-1,4'-2H-3',1'-benzoxazin)-2'-oxo-1-yl]-1,1-dimethyl-propylamino}-1-hydroxy-ethyl)-phenyl]-methanesulphonamide are hydrogenated analogously to Example 7b. After separation of the catalyst the filtrate is freed from the solvent, combined with 8 mL ethyl acetate and acidified to pH 2 by the addition of hydrochloric acid in ethyl acetate. The solvent is distilled off and the residue is stirred in diethyl ether and filtered. Yield: 40 mg (23%, hydrochloride); mass spectroscopy: [M+H]$^+$=532; HPLC: R$_f$=11.8 minutes (method A).

The (R)- and (S)-enantiomers of this embodiment may be obtained by common methods known in the art. Particular importance attaches to the (R)-enantiomer of this embodiment according to the invention.

Example 9

N-[5-(2-{1,1-dimethyl-3-[spiro(cyclopropyl-1,4'-2H-3',1'-benzoxazin)-2'-oxo-1-yl]-propylamino}-1-hydroxy-ethyl)-2-hydroxy-phenyl]-methanesulphonamide

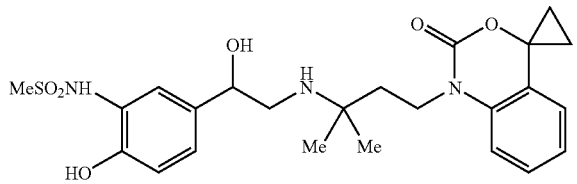

a) N-[2-benzyloxy-5-(2-{3-[spiro(cyclopropyl-1,4'-2H-3',1'-benzoxazin)-2'-oxo-1-yl]-1,1-dimethyl-propylamino}-1-hydroxy-ethyl]-phenyl]-methanesulphonamide: 292 mg (0.77 m mol) N-[2-benzyloxy-5-(2-ethoxy-2-hydroxy-acetyl)-phenyl]-methanesulphonamide and 200 mg (0.77 mmol) 1-(3-amino-3-methyl-butyl)-spiro(cyclopropyl-1,4'-2H-3',1'-benzoxazin)-2'-one are reacted and worked up analogously to Example 7a. The crude product is combined with 8 mL ethyl acetate and acidified to pH 2 with hydrochloric acid in ethyl acetate. The solvent is distilled off and the residue is stirred in diethyl ether. Yield: 400 mg (84%, hydrochloride), HPLC: R$_f$=15.2 minutes (method A).

b) N-[5-(2-{1,1-dimethyl-3-[spiro(cyclopropyl-1,4'-2H-3',1'-benzoxazin)-2'-oxo-1-yl]-propylamino}-1-hydroxy-ethyl)-2-hydroxy-phenyl]-methanesulphonamide: the product is prepared analogously to Example 1 b from 400 mg (0.65 mmol) N-[2-benzyloxy-5-(2-{3-[spiro(cyclopropyl-1,4'-2H-3',1'-benzoxazin)-2'-oxo-1-yl]-1,1-dimethyl-propylamino}-1-hydroxy-ethyl]-phenyl]-methanesulphonamide hydrochloride. Yield: 230 mg (67%, hydrochloride); mass spectroscopy: [M+H]$^+$=490; HPLC: R$_f$=8.9 minutes (method A).

The (R)- and (S)-enantiomers of this embodiment may be obtained by common methods known in the art. Particular importance attaches to the (R)-enantiomer of this embodiment according to the invention.

Example 10

N-(5-{2-[3-(4,4-diethyl-2-oxo-4H-benzo[d][1,3]oxazin-1-yl)-1,1-dimethyl-propylamino]-1-hydroxy-ethyl}-2-hydroxy-phenyl)-methanesulphonamide

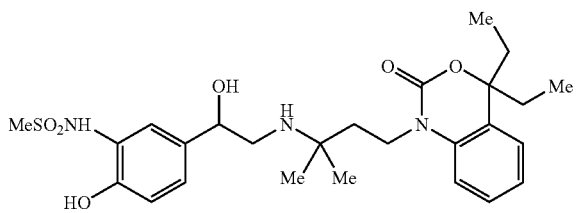

379 mg (1 mmol) N-[2-benzyloxy-5-(2-ethoxy-2-hydroxy-acetyl)-phenyl]-methanesulphonamide and 290 mg (1 mmol) 1-(3-amino-3-methyl-butyl)-4,4-diethyl-1,4-dihydrobenzo[d][1,3]oxazin-2-on are suspended in 5 mL ethanol and heated to 70° C. The resulting solution is stirred for one hour at 70° C. and then cooled to ambient temperature. After the addition of 113 mg (3 mmol) sodium borohydride the mixture is stirred for 3 hours at ambient temperature, combined with 0.7 mL saturated potassium carbonate solution and stirred for a further 30 minutes. The mixture is filtered through aluminium oxide (basic), washed repeatedly with dichloromethane/methanol (15:1) and evaporated down. The crude product thus obtained is purified by chromatography (dichloromethane with 0-10% methanol/ammonia=9:1). The benzylether thus obtained is dissolved in 10 mL methanol and hydrogenated with palladium on charcoal as catalyst at 1 bar hydrogen pressure. Then the catalyst is filtered off and the filtrate is evaporated down. White solid. Yield: 338 mg (65% over 2 steps); mass spectroscopy: [M+H]$^+$=520.

The (R)- and (S)-enantiomers of this embodiment may be obtained by common methods known in the art. Particular importance attaches to the (R)-enantiomer of this embodiment according to the invention. The angle of rotation of (R)-N-(5-{2-[3-(4,4-diethyl-2-oxo-4H-benzo[d][1,3]oxazin-1-yl)-1,1-dimethyl-propylamino]-1-hydroxy-ethyl}-2-hydroxy-phenyl)-methanesulphonamide hydrochloride (cocrystallised with a molecule of acetone) is −28.8° (c=1%, in methanol at 20° C.).

N-(5-{(R)-2-[3-(4,4-diethyl-2-oxo-4H-benzo[d][1,3]oxazin-1-yl)-1,1-dimethyl-propylamino]-1-hydroxy-ethyl}-2-hydroxy-phenyl)-methanesulphonamide (free base, crystalline)

2.50 g (4.81 mmol) N-(5-{(R)-2-[3-(4,4-diethyl-2-oxo-4H-benzo[d][1,3]oxazin-1-yl)-1,1-dimethyl-propylamino]-1-hydroxy-ethyl}-2-hydroxy-phenyl)-methanesulphonamide are heated in 250 mL methanol. Activated charcoal is added and the mixture is filtered hot through kieselguhr. Then the solution is evaporated down to 50 mL and slowly cooled. The precipitated solid is suction filtered and washed with methanol and diethyl ether. Yield: 1.11 g; mass spectroscopy [M+H]$^+$=520; melting point=168° C.

Example 11

N-(5-{2-[3-(4,4-diethyl-6-fluoro-2-oxo-4H-benzo[d][1,3]oxazin-1-yl)-1,1-dimethyl-propylamino]-1-hydroxy-ethyl}-2-hydroxy-phenyl)-methanesulphonamide

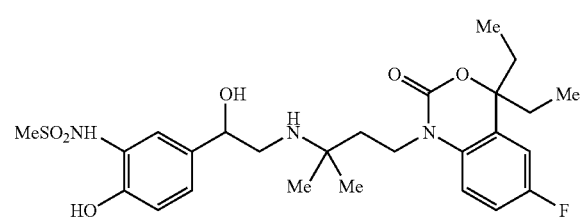

a) N-(2-benzyloxy-5-{2-[3-(4,4-diethyl-6-fluoro-2-oxo-4H-benzo[d][1,3]oxazin-1-yl)-1,1-dimethyl-propylamino]-1-hydroxy-ethyl}-phenyl)-methanesulphonamide: Reaction of 246 mg (0.65 mmol) N-[2-benzyloxy-5-(2-ethoxy-2-hydroxy-acetyl)-phenyl]-methanesulphonamide and 200 mg (0.65 mmol) 1-(3-amino-3-methyl-butyl)-4,4-diethyl-6-fluoro-1,4-dihydro-benzo[D][1,3]oxazin-2-one analogously to Example 7a. One difference is that the preparation of the hydrochloride is omitted. Instead, the free base is purified by chromatography (reverse phase, acetonitrile/water gradient with 0.1% trifluoroacetic acid).

Yield: 180 mg (trifluoroacetate), HPLC: R$_t$=17.4 minutes (method A).

b) N-(5-{2-[3-(4,4-diethyl-6-fluoro-2-oxo-4H-benzo[d][1,3]oxazin-1-yl)-1,1-dimethyl-propylamino]-1-hydroxy-ethyl}-2-hydroxy-phenyl)-methanesulphonamide: 175 mg of —N-(2-benzyloxy-5-{2-[3-(4,4-diethyl-6-fluoro-2-oxo-4H-benzo[d][1,3]oxazin-1-yl)-1,1-dimethyl-propylamino]-1-hydroxy-ethyl}-phenyl)-methanesulphonamide trifluoroacetate in 9 mL methanol are hydrogenated in the presence of 40 mg Raney nickel at ambient temperature and 3 bar hydrogen pressure. The catalyst is filtered off and the filtrate is freed from the solvent.

Yield: 131 mg (trifluoroacetate); mass spectroscopy: [M+H]$^+$=538.

The (R)- and (S)-enantiomers of this embodiment may be obtained by common methods known in the art. Particular importance attaches to the (R)-enantiomer of this embodiment according to the invention.

Example 12

N-(5-{2-[3-(4,4-diethyl-7-fluoro-2-oxo-4H-benzo[d][1,3]oxazin-1-yl)-1,1-dimethyl-propylamino]-1-hydroxy-ethyl}-2-hydroxy-phenyl)-methanesulphonamide

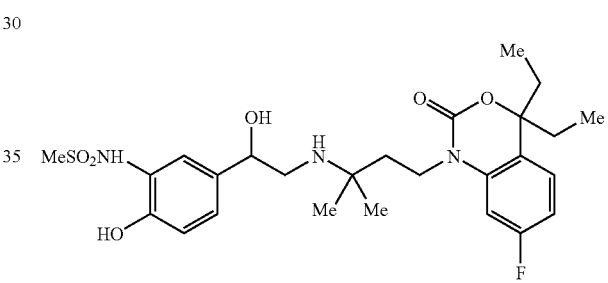

a) N-(2-benzyloxy-5-{2-[3-(4,4-diethyl-7-fluoro-2-oxo-4H-benzo[d][1,3]oxazin-1-yl)-1,1-dimethyl-propylamino]-1-hydroxy-ethyl}-phenyl)-methanesulphonamide: 246 mg (0.65 mmol) N-[2-benzyloxy-5-(2-ethoxy-2-hydroxy-acetyl)-phenyl]-methanesulphonamide and 200 mg (0.65 mmol) 1-(3-amino-3-methyl-butyl)-4,4-diethyl-7-fluoro-1,4-dihydro-benzo[d][1,3]oxazin-2-one are reacted and worked up analogously to Example 7a. A difference is that the production of the hydrochloride is omitted and the free base is purified by chromatography (reverse phase, acetonitrile/water gradient with 0.1% trifluoroacetic acid).

Yield: 220 mg (trifluoroacetate), HPLC: R$_t$=17.7 minutes (method A).

b) N-(5-{2-[3-(4,4-diethyl-7-fluoro-2-oxo-4H-benzo[d][1,3]oxazin-1-yl)-1,1-dimethyl-propylamino]-1-hydroxy-ethyl}-2-hydroxy-phenyl)-methanesulphonamide: Prepared analogously to Example 11b from 210 mg of N-(2-benzyloxy-5-{2-[3-(4,4-diethyl-7-fluoro-2-oxo-4H-benzo[d][1,3]oxazin-1-yl)-1,1-dimethyl-propylamino]-1-hydroxy-ethyl}-phenyl)-methanesulphonamide trifluoroacetate.

Yield: 154 mg (trifluoroacetate); mass spectroscopy: [M+H]$^+$=538.

The (R)- and (S)-enantiomers of this embodiment may be obtained by common methods known in the art. Particular importance attaches to the (R)-enantiomer of this embodiment according to the invention.

Example 13

N-(5-{2-[3-(4,4-diethyl-8-methoxy-2-oxo-4H-benzo[d][1,3]oxazin-1-yl)-1,1-dimethyl-propylamino]-1-hydroxy-ethyl}-2-hydroxy-phenyl)-methanesulphonamide

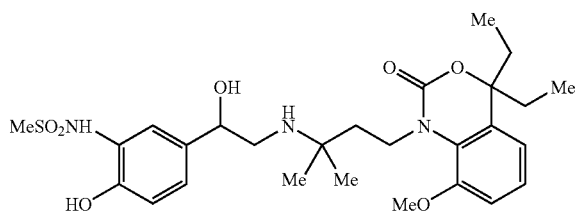

a) N-(2-benzyloxy-5-{2-[3-(4,4-diethyl-8-methoxy-2-oxo-4H-benzo[d][1,3]oxazin-1-yl)-1,1-dimethyl-propylamino]-1-hydroxy-ethyl}-phenyl)-methanesulphonamide: reaction of 237 mg (0.625 mmol) N-[2-benzyloxy-5-(2-ethoxy-2-hydroxy-acetyl)-phenyl]-methanesulphonamide and 200 mg (0.624 mmol) 1-(3-amino-3-methyl-butyl)-4,4-diethyl-8-methoxy-1,4-dihydro-benzo[d][1,3]oxazin-2-one analogously to Example 7a. The crude product is dissolved in ethyl acetate and acidified to pH 2 with hydrochloric acid in ethyl acetate. The solvent is distilled off and the residue is stirred in diethyl ether. Then the hydrochloride thus obtained (330 mg) is further purified by chromatography.

Yield: 90 mg (trifluoroacetate), HPLC: $R_t$=17.6 minutes (method A).

b) N-(5-{2-[3-(4,4-diethyl-8-methoxy-2-oxo-4H-benzo[d][1,3]oxazin-1-yl)-1,1-dimethyl-propylamino]-1-hydroxy-ethyl}-2-hydroxy-phenyl)-methanesulphonamide: 80 mg (0.118 mmol) N-(2-benzyloxy-5-{2-[3-(4,4-diethyl-8-methoxy-2-oxo-4H-benzo[d][1,3]oxazin-1-yl)-1,1-dimethyl-ethyl-propylamino]-1-hydroxy-ethyl}-phenyl)-methanesulphonamide trifluoroacetate are hydrogenated analogously to Example 11b. Yield: 70 mg (trifluoroacetate); mass spectroscopy: [M+H]$^+$=550.

The (R)- and (S)-enantiomers of this embodiment may be obtained by common methods known in the art. Particular importance attaches to the (R)-enantiomer of this embodiment according to the invention.

Example 14

N-(5-{2-[3-(4,4-diethyl-6-methoxy-2-oxo-4H-benzo[d][1,3]oxazin-1-yl)-1,1-dimethyl-propylamino]-1-hydroxy-ethyl}-2-hydroxy-phenyl)-methanesulphonamide

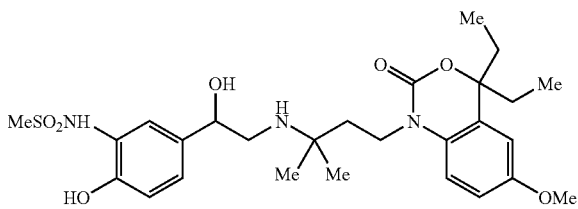

a) N-(2-benzyloxy-5-{2-[3-(4,4-diethyl-6-methoxy-2-oxo-4H-benzo[d][1,3]oxazin-1-yl)-1,1-dimethyl-propylamino]-1-hydroxy-ethyl}-phenyl)-methanesulphonamide: 235 mg (0.619 mmol) N-[2-benzyloxy-5-(2-ethoxy-2-hydroxy-acetyl)-phenyl]-methanesulphonamide and 200 mg (0.624 mmol) 1-(3-amino-3-methyl-butyl)-4,4-diethyl-6-methoxy-1,4-dihydro-benzo[d][1,3]oxazin-2-one are reacted analogously to Example 7a. One difference is that the crude product is not precipitated as the hydrochloride, but purified by chromatography (reverse phase, acetonitrile/water gradient with 0.1% trifluoroacetic acid).

Yield: 150 mg (trifluoroacetate), HPLC: $R_t$=16.9 minutes (method A).

b) N-(5-{2-[3-(4,4-diethyl-6-methoxy-2-oxo-4H-benzo[d][1,3]oxazin-1-yl)-1,1-dimethyl-propylamino]-1-hydroxy-ethyl}-2-hydroxy-phenyl)-methanesulphonamide: The target compound is prepared from N-(2-benzyloxy-5-{2-[3-(4,4-diethyl-6-methoxy-2-oxo-4H-benzo[d][1,3]oxazin-1-yl)-1,1-dimethyl-propylamino]-1-hydroxy-ethyl}-phenyl)-methanesulphonamide trifluoroacetate analogously to Example 11b. Grey solid. Mass spectroscopy: [M+H]$^+$=550.

The (R)- and (S)-enantiomers of this embodiment may be obtained by common methods known in the art. Particular importance attaches to the (R)-enantiomer of this embodiment according to the invention.

Synthesis of Salts

The compounds of formula 1 may generally be prepared using the following method.

a) hydrobromide: 1.02 mmol of the free base of the compound of formula 1 are suspended in 3 mL acetone and combined with 170 µL (1.01 mmol) 48% hydrobromic acid in 1 mL acetone. Sufficient diethyl ether is added to the resulting solution to cause a yellow oil to be precipitated. The oil is separated off, dissolved in 2 mL acetone, diluted with a little ethyl acetate and mixed with a crystallisation aid. The salt precipitated is filtered off and washed with ethyl acetate and diethyl ether. The solid is then recrystallised from acetonitrile. Yield: approx. 75%, melting point: 145±5° C.

b) hydrochloride: 2.05 mmol of the free base of the compound of formula 1 are suspended in 7 mL acetone and combined with 506 µl (2.02 mmol) 4 molar hydrochloric acid in 550 µl acetone, whereupon a clear solution is formed. After the addition of a crystallisation aid a total of 7 mL diethyl ether are added dropwise. The precipitated solid is separated off after 3 hours, washed with diethyl ether and dried at 40° C. Then the solid is recrystallised from acetonitrile with the addition of a few drops of water, filtered and again washed with diethyl ether. Yield: 46%, melting point: 162±3° C.

c) hydrochloride: 1.92 mmol of the free base of the compound of formula 1 are suspended in 7 mL acetone and combined with 200 µl (1.76 mmol) 32% hydrochloric acid in 1 mL acetone. A clear solution is formed, from which a solid is precipitated after the addition of a crystallisation aid. The solution is diluted with diethyl ether and filtered. The solid is washed with acetone/diethyl ether and recrystallised from acetonitrile. Yield: 73%.

The compounds specified below may be prepared by the methods described herein before:

Example 1.1a

N-(5-{2-[1,1-dimethyl-3-(4-methyl-2-oxo-4H-benzo[d][1,3]oxazin-1-yl)-propylamino]-1-hydroxy-ethyl}-2-hydroxy-phenyl)-methanesulphonamide hydrobromide Example 1.2a N-(5-{2-[1,1-dimethyl-3-(2-oxo-4H-benzo[d][1,3]oxazin-1-yl)-propylamino]-1-hydroxy-ethyl}-2-hydroxy-phenyl)-methanesulphonamide hydrobromide Example 1.3a N-(5-{2-[3-(4-ethyl-2-oxo-4H-benzo[d][1,3]oxazin-1-yl)-1,1-dimethyl-propylamino]-1-hydroxy-ethyl}-2-hydroxy-phenyl)-methanesulphonamide hydrobromide Example 1.4a N-(5-{2-[3-(4,4-dimethyl-2-oxo-4H-benzo[d][1,3]oxazin-1-yl)-1,1-dimethyl-propylamino]-1-hydroxy-ethyl}-2-hydroxy-phenyl)-methanesulphonamide hydrobromide Example 1.5a N-(2-hydroxy-5-{1-hydroxy-2-[3-(6-hydroxy-4,4-dimethyl-2-oxo-4H-benzo[d][1,3]oxazin-1-yl)-1,1-dimethyl-propylamino]-ethyl}-phenyl)-methanesulphonamide hydrobromide Example 1.6a N-(2-hydroxy-5-{1-hydroxy-2-[3-(6-methoxy-4,4-dimethyl-2-oxo-4H-benzo[d][1,3]oxazin-1-yl)-1,1-dimethyl-propylamino]-ethyl}-phenyl)-methanesulphonamide hydrobromide Example 1.7a N-(5-{2-[1,1-dimethyl-3-(2-oxo-4,4-dipropyl-4H-benzo[d][1,3]oxazin-1-yl)-propylamino]-1-hydroxy-ethyl}-2-hydroxy-phenyl)-methanesulphonamide hydrobromide Example 1.8a N-[5-(2-{1,1-dimethyl-3-[spiro(cyclohexane-1,4'-2H-3',1'-benzoxazin)-2'-oxo-1-yl]-propylamino}-1-hydroxy-ethyl)-2-hydroxy-phenyl]-methanesulphonamide hydrobromide Example 1.9a N-[5-(2-{1,1-dimethyl-3-[spiro(cyclopropyl-1,4'-2H-3',1'-benzoxazin)-2'-oxo-1-yl]-propylamino}-1-hydroxy-ethyl)-2-hydroxy-phenyl]-methanesulphonamide hydrobromide Example 1.10a N-(5-{2-[3-(4,4-diethyl-2-oxo-4H-benzo[d][1,3]oxazin-1-yl)-1,1-dimethyl-propylamino]-1-hydroxy-ethyl}-2-hydroxy-phenyl)-methanesulphonamide hydrobromide Example 1.11a N-(5-{2-[3-(4,4-diethyl-6-fluoro-2-oxo-4H-benzo[d][1,3]oxazin-1-yl)-1,1-dimethyl-propylamino]-1-hydroxy-ethyl}-2-hydroxy-phenyl)-methanesulphonamide hydrobromide Example 1.12a N-(5-{2-[3-(4,4-diethyl-7-fluoro-2-oxo-4H-benzo[d][1,3]oxazin-1-yl)-1,1-dimethyl-propylamino]-1-hydroxy-ethyl}-2-hydroxy-phenyl)-methanesulphonamide hydrobromide Example 1.13a N-(5-{2-[3-(4,4-diethyl-8-methoxy-2-oxo-4H-benzo[d][1,3]oxazin-1-yl)-1,1-dimethyl-propylamino]-1-hydroxy-ethyl}-2-hydroxy-phenyl)-methanesulphonamide hydrobromide Example 1.14a N-(5-{2-[3-(4,4-diethyl-6-methoxy-2-oxo-4H-benzo[d][1,3]oxazin-1-yl)-1,1-dimethyl-propylamino]-1-hydroxy-ethyl}-2-hydroxy-phenyl)-methanesulphonamide hydrobromide Example 1.1b N-(5-{2-[1,1-dimethyl-3-(4-methyl-2-oxo-4H-benzo[d][1,3]oxazin-1-yl)-propylamino]-1-hydroxy-ethyl}-2-hydroxy-phenyl)-methanesulphonamide hydrochloride Example 1.2b N-(5-{2-[1,1-dimethyl-3-(2-oxo-4H-benzo[d][1,3]oxazin-1-yl)-propylamino]-1-hydroxy-ethyl}-2-hydroxy-phenyl)-methanesulphonamide hydrochloride Example 1.3b N-(5-{2-[3-(4-ethyl-2-oxo-4H-benzo[d][1,3]oxazin-1-yl)-1,1-dimethyl-propylamino]-1-hydroxy-ethyl}-2-hydroxy-phenyl)-methanesulphonamide hydrochloride Example 1.4b N-(5-{2-[3-(4,4-dimethyl-2-oxo-4H-benzo[d][1,3]oxazin-1-yl)-1,1-dimethyl-propylamino]-1-hydroxy-ethyl}-2-hydroxy-phenyl)-methanesulphonamide hydrochloride Example 1.5b N-(2-hydroxy-5-{1-hydroxy-2-[3-(6-hydroxy-4,4-dimethyl-2-oxo-4H-benzo[d][1,3]oxazin-1-yl)-1,1-dimethyl-propylamino]-ethyl}-phenyl)-methanesulphonamide hydrochloride Example 1.6b N-(2-hydroxy-5-{1-hydroxy-2-[3-(6-methoxy-4,4-dimethyl-2-oxo-4H-benzo[d][1,3]oxazin-1-yl)-1,1-dimethyl-propylamino]-ethyl}-phenyl)-methanesulphonamide hydrochloride

Example 1.7b

N-(5-{2-[1,1-dimethyl-3-(2-oxo-4,4-dipropyl-4H-benzo[d][1,3]oxazin-1-yl)-propylamino]-1-hydroxy-ethyl}-2-hydroxy-phenyl)-methanesulphonamide hydrochloride

Example 1.8b

N-[5-(2-{1,1-dimethyl-3-[spiro(cyclohexane-1,4'-2H-3',1'-benzoxazin)-2'-oxo-1-yl]-propylamino}-1-hydroxy-ethyl)-2-hydroxy-phenyl]-methanesulphonamide hydrochloride

Example 1.9b

N-[5-(2-{1,1-dimethyl-3-[spiro(cyclopropyl-1,4'-2H-3',1'-benzoxazin)-2'-oxo-1-yl]-propylamino}-1-hydroxy-ethyl)-2-hydroxy-phenyl]-methanesulphonamide hydrochloride

Example 1.10b

N-(5-{2-[3-(4,4-diethyl-2-oxo-4H-benzo[d][1,3]oxazin-1-yl)-1,1-dimethyl-propylamino]-1-hydroxy-ethyl}-2-hydroxy-phenyl)-methanesulphonamide hydrochloride

Example 1.11b

N-(5-{2-[3-(4,4-diethyl-6-fluoro-2-oxo-4H-benzo[d][1,3]oxazin-1-yl)-1,1-dimethyl-propylamino]-1-hydroxy-ethyl}-2-hydroxy-phenyl)-methanesulphonamide hydrochloride

Example 1.12b

N-(5-{2-[3-(4,4-diethyl-7-fluoro-2-oxo-4H-benzo[d][1,3]oxazin-1-yl)-1,1-dimethyl-propylamino]-1-hydroxy-ethyl}-2-hydroxy-phenyl)-methanesulphonamide hydrochloride

Example 1.13b

N-(5-{2-[3-(4,4-diethyl-8-methoxy-2-oxo-4H-benzo[d][1,3]oxazin-1-yl)-1,1-dimethyl-propylamino]-1-hydroxy-ethyl}-2-hydroxy-phenyl)-methanesulphonamide hydrochloride

Example 1.14b

N-(5-{2-[3-(4,4-diethyl-6-methoxy-2-oxo-4H-benzo[d][1,3]oxazin-1-yl)-1,1-dimethyl-propylamino]-1-hydroxy-ethyl}-2-hydroxy-phenyl)-methanesulphonamide hydrochloride The R-enantiomers of the compounds 1.1a, 1.2a, 1.3a, 1.4a, 1.5a, 1.6a, 1.7a, 1.8a, 1.9a, 1.10a, 1.11a, 1.12a, 1.13a, 1.14a and 1.1b, 1.2b, 1.3b, 1.4b, 1.5b, 1.6b, 1.7b, 1.8b, 1.9b, 1.10b, 1.11b, 1.12b, 1.13b, 1.14b are preferred.

X-Ray Powder Diagrams for Example 10 and the Salts Thereof

Parameters of the X-ray powder diffractometer used for the measurement: STOE Stadi P X-ray powder diffractometer with location-sensitive detector in transmission mode with curved germanium (111) primary monochromator; wavelength used: CuK$_{\alpha 1}$ with λ=1.540598 Å; power absorption of the X-ray tube: 40 kV, 40 mA; absorption range: 3-40° 2Θ.

Figure 2:
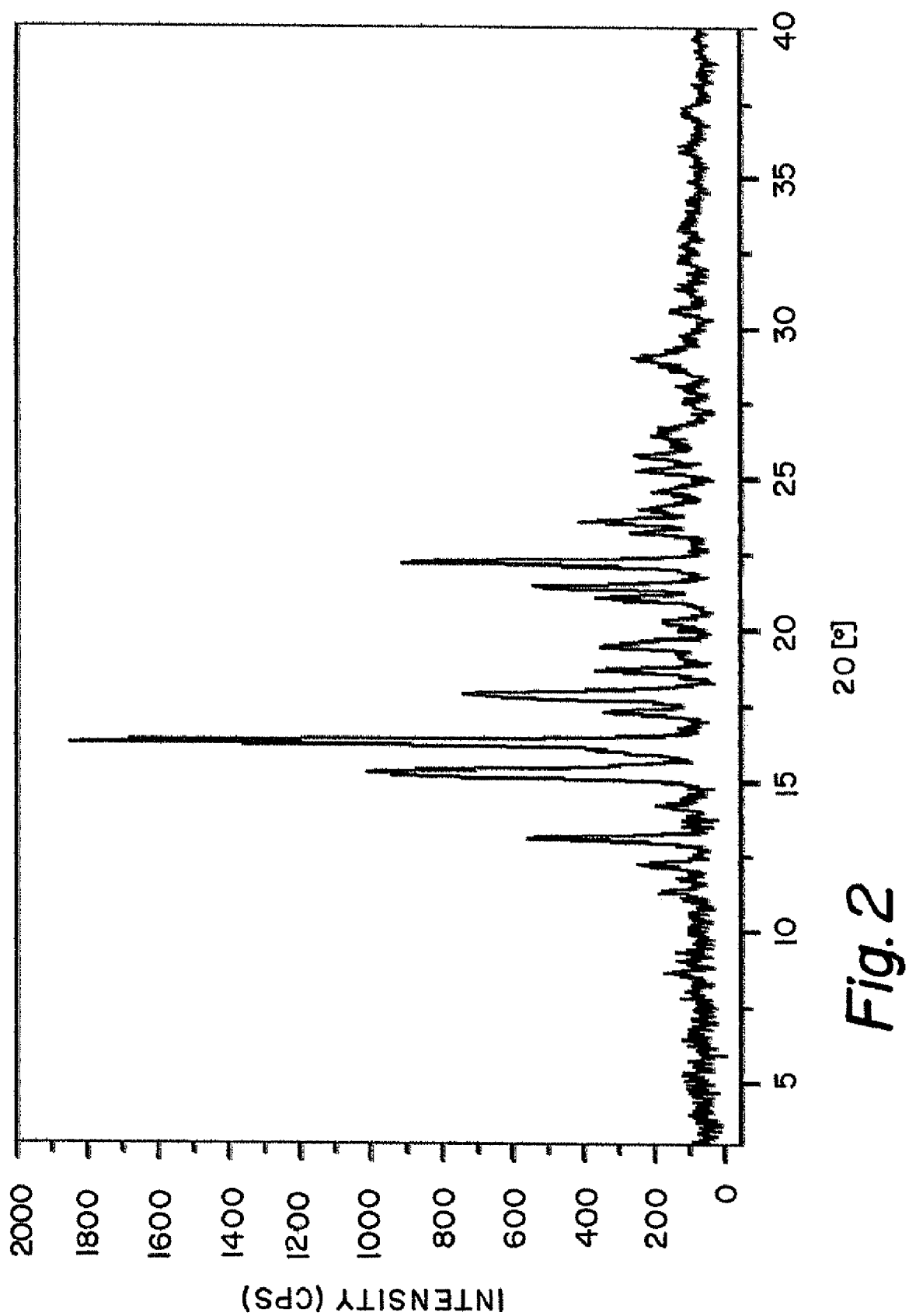
Figure 3:
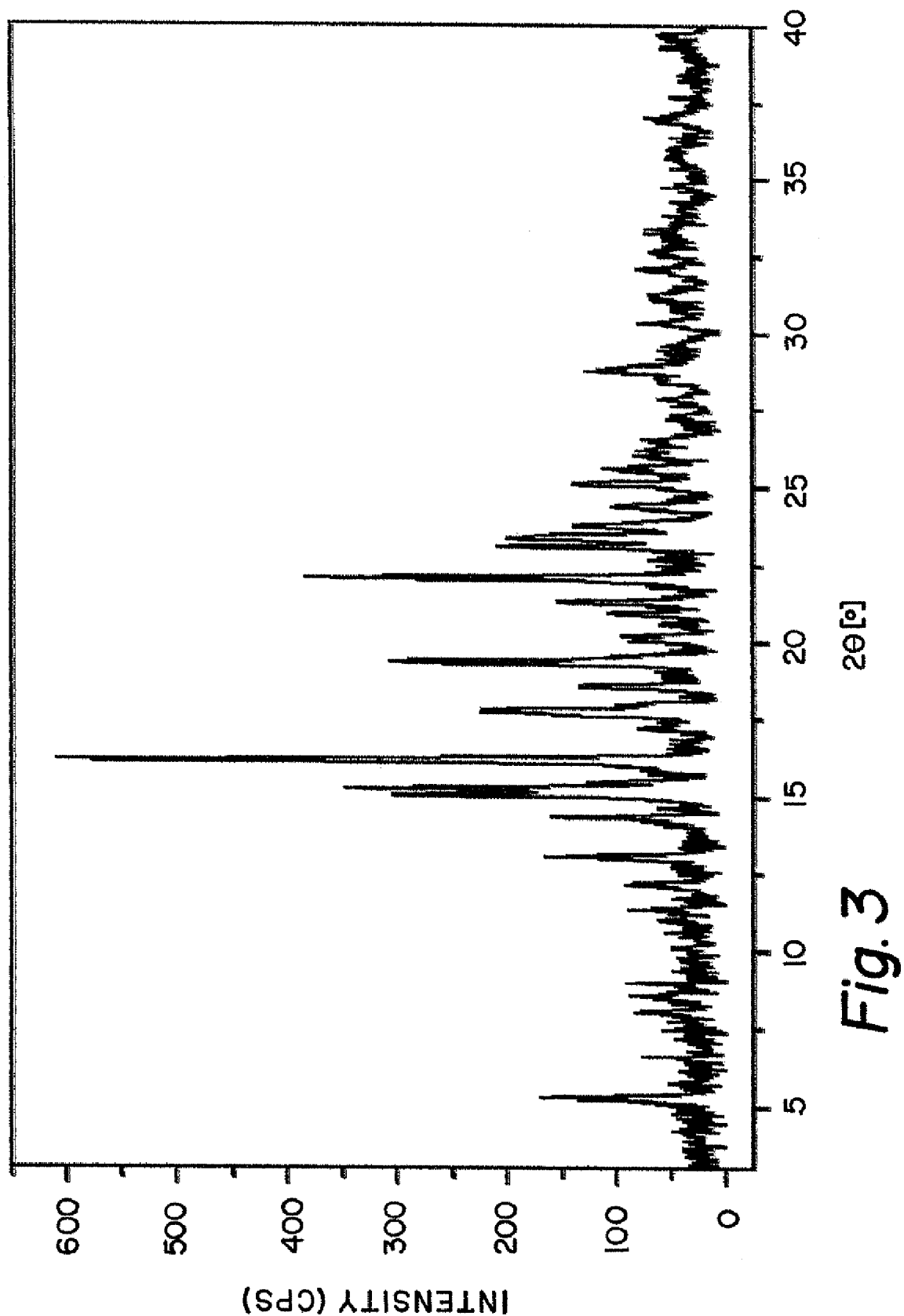

The following Tables show the characteristic X-ray reflections with intensities (standardised, up to 40° 2Θ) for the Examples specified. The corresponding diagrams (FIGS. 1-3) can be found in the Appendix in the Figures section.

FIG. 1: X-ray powder diagram of the free base of N-(5-{(R)-2-[3-(4,4-diethyl-2-oxo-4H-benzo[d][1,3]oxazin-1-yl)-1,1-dimethyl-propylamino]-1-hydroxy-ethyl}-2-hydroxy-phenyl)-methanesulphonamide FIG. 2: X-ray powder diagram of the monohydrochloride of N-(5-{(R)-2-[3-(4,4-diethyl-2-oxo-4H-benzo[d][1,3]oxazin-1-yl)-1,1-dimethyl-propylamino]-1-hydroxy-ethyl}-2-hydroxy-phenyl)-methanesulphonamide FIG. 3: X-ray powder diagram of the monohydrobromide of N-(5-{(R)-2-[3-(4,4-diethyl-2-oxo-4H-benzo[d][1,3]oxazin-1-yl)-1,1-dimethyl-propylamino]-1-hydroxy-ethyl}-2-hydroxy-phenyl)-methanesulphonamide As the skilled man knows, the intensities of the reflections may vary depending on the preparation of the samples. The intensities specified below were found on measuring the above-mentioned Example and cannot be transferred to any other measurement.

TABLE 1

X-ray reflections (up to 30° 2Θ) with intensities (standardised) of the free base of N-(5-{(R)-2-[3-(4,4-diethyl-2-oxo-4H-benzo[d][1,3]oxazin-1-yl)-1,1-dimethyl-propylamino]-1-hydroxy-ethyl}-2-hydroxy-phenyl)-methanesulphonamide

| 2Θ [°] | $d_{hkl}$ [Å] | intensity I/I$_o$ [%] |
|---|---|---|
| 4.76 | 18.56 | 77 |
| 9.53 | 9.27 | 7 |
| 10.86 | 8.14 | 100 |
| 11.31 | 7.82 | 13 |
| 11.85 | 7.46 | 4 |
| 12.52 | 7.07 | 5 |
| 13.22 | 6.69 | 4 |
| 14.01 | 6.31 | 69 |
| 14.28 | 6.20 | 7 |
| 14.71 | 6.02 | 26 |
| 14.94 | 5.93 | 24 |
| 15.29 | 5.79 | 17 |
| 15.69 | 5.64 | 21 |
| 16.20 | 5.47 | 8 |
| 16.73 | 5.29 | 8 |
| 17.40 | 5.09 | 8 |
| 18.06 | 4.91 | 6 |
| 18.81 | 4.71 | 22 |
| 19.11 | 4.64 | 5 |
| 19.62 | 4.52 | 12 |
| 20.43 | 4.34 | 21 |
| 20.69 | 4.29 | 20 |
| 20.89 | 4.25 | 16 |
| 21.42 | 4.15 | 15 |
| 21.80 | 4.07 | 15 |
| 22.22 | 4.00 | 8 |
| 22.72 | 3.91 | 35 |
| 23.26 | 3.82 | 25 |
| 23.53 | 3.78 | 6 |
| 23.89 | 3.72 | 7 |
| 24.01 | 3.70 | 7 |
| 24.15 | 3.68 | 5 |
| 24.52 | 3.63 | 8 |
| 25.07 | 3.55 | 10 |
| 25.46 | 3.50 | 6 |
| 25.95 | 3.43 | 5 |
| 26.09 | 3.41 | 6 |
| 26.59 | 3.35 | 4 |
| 27.08 | 3.29 | 5 |
| 27.92 | 3.19 | 5 |
| 28.57 | 3.12 | 3 |
| 29.32 | 3.04 | 5 |
| 30.13 | 2.96 | 4 |

TABLE 2

X-ray reflections (up to 30° 2Θ) with intensities (standardised) of the mono-hydrochloride of N-(5-{(R)-2-[3-(4,4-diethyl-2-oxo-4H-benzo[d][1,3]oxazin-1-yl)-1,1-dimethyl-propylamino]-1-hydroxy-ethyl}-2-hydroxy-phenyl)-methanesulphonamide

| 2Θ [°] | $d_{hkl}$ [Å] | intensity $I/I_o$ [%] |
|---|---|---|
| 5.31 | 16.62 | 3 |
| 6.65 | 13.29 | 2 |
| 8.64 | 10.23 | 5 |
| 9.04 | 9.78 | 3 |
| 9.31 | 9.49 | 3 |
| 10.14 | 8.71 | 2 |
| 11.38 | 7.77 | 6 |
| 11.77 | 7.51 | 4 |
| 12.25 | 7.22 | 9 |
| 13.12 | 6.74 | 27 |
| 13.67 | 6.47 | 2 |
| 14.19 | 6.24 | 5 |
| 14.41 | 6.14 | 3 |
| 15.20 | 5.82 | 42 |
| 15.32 | 5.78 | 48 |
| 16.05 | 5.52 | 17 |
| 16.30 | 5.43 | 100 |
| 16.82 | 5.27 | 3 |
| 17.31 | 5.12 | 14 |
| 17.87 | 4.96 | 37 |
| 18.69 | 4.74 | 17 |
| 19.18 | 4.62 | 4 |
| 19.49 | 4.55 | 16 |
| 20.34 | 4.36 | 8 |
| 21.07 | 4.21 | 16 |
| 21.45 | 4.14 | 29 |
| 22.24 | 3.99 | 50 |
| 23.23 | 3.83 | 11 |
| 23.58 | 3.77 | 17 |
| 23.98 | 3.71 | 9 |
| 24.62 | 3.61 | 6 |
| 25.30 | 3.52 | 10 |
| 25.79 | 3.45 | 10 |
| 26.44 | 3.37 | 7 |
| 26.67 | 3.34 | 5 |
| 27.49 | 3.24 | 2 |
| 28.10 | 3.17 | 4 |
| 28.69 | 3.11 | 6 |
| 29.03 | 3.07 | 10 |
| 29.81 | 2.99 | 3 |
| 30.56 | 2.92 | 4 |

TABLE 3

X-ray reflections (up to 30° 2Θ) with intensities (standardised) of the mono-hydrobromide of the free base of N-(5-{(R)-2-[3-(4,4-diethyl-2-oxo-4H-benzo[d][1,3]oxazin-1-yl)-1,1-dimethyl-propylamino]-1-hydroxy-ethyl}-2-hydroxy-phenyl)-methanesulphonamide

| 2Θ [°] | $d_{hkl}$ [Å] | intensity $I/I_o$ [%] |
|---|---|---|
| 5.27 | 16.75 | 25 |
| 6.60 | 13.39 | 6 |
| 8.05 | 10.98 | 11 |
| 8.56 | 10.32 | 11 |
| 8.97 | 9.85 | 9 |
| 10.57 | 8.36 | 6 |
| 10.96 | 8.06 | 8 |
| 11.30 | 7.82 | 10 |
| 12.13 | 7.29 | 12 |
| 13.01 | 6.80 | 24 |
| 14.33 | 6.18 | 24 |
| 15.04 | 5.89 | 43 |
| 15.24 | 5.81 | 55 |
| 15.45 | 5.73 | 18 |
| 16.17 | 5.48 | 100 |
| 17.19 | 5.15 | 10 |
| 17.76 | 4.99 | 29 |
| 17.94 | 4.94 | 10 |
| 18.54 | 4.78 | 18 |
| 19.34 | 4.59 | 48 |
| 20.05 | 4.42 | 10 |
| 20.18 | 4.40 | 13 |
| 20.94 | 4.24 | 15 |
| 21.28 | 4.17 | 21 |
| 22.06 | 4.03 | 58 |
| 23.10 | 3.85 | 30 |
| 23.37 | 3.80 | 30 |
| 23.76 | 3.74 | 20 |
| 24.38 | 3.65 | 14 |
| 25.11 | 3.54 | 20 |
| 25.59 | 3.48 | 14 |
| 26.01 | 3.42 | 9 |
| 26.21 | 3.40 | 8 |
| 26.42 | 3.37 | 6 |
| 26.56 | 3.35 | 7 |
| 27.29 | 3.26 | 6 |
| 27.83 | 3.20 | 8 |
| 28.42 | 3.14 | 7 |
| 28.77 | 3.10 | 18 |
| 30.34 | 2.94 | 9 |

Thermoanalyis (DSC/TG) for Example 10 and the Salts Thereof

Technical data relating to the thermoanalytical DSC device used: DSC 822 made by Mettler Toledo; heating rate: 10 K/min; type of crucible: perforated aluminium crucible; atmosphere: $N_2$, 80 ml/min flux; typical weight: 3-10 mg.

Technical data relating to the thermoanalytical TG device used: TGA/SDTA 851 made by Mettler Toledo with IR coupling (Nicolet FT-IR 4700) for analysing the volatile fractions driven off; heating rate: 10 K/min; type of crucible: open aluminium oxide crucible; atmosphere: $N_2$, 20 ml/min flux; typical weight: 15-25 mg.

Figure 5:
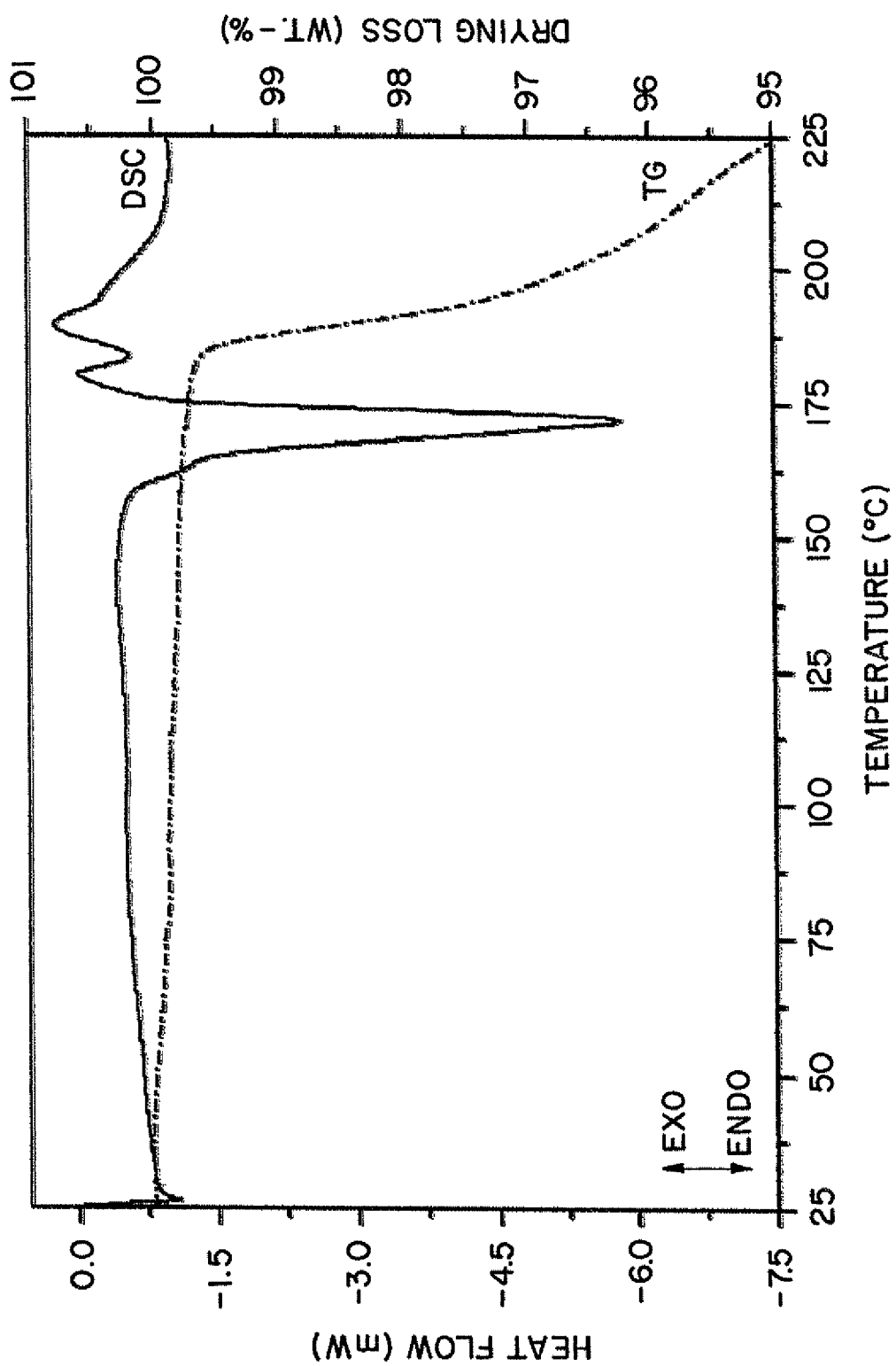
Figure 6:
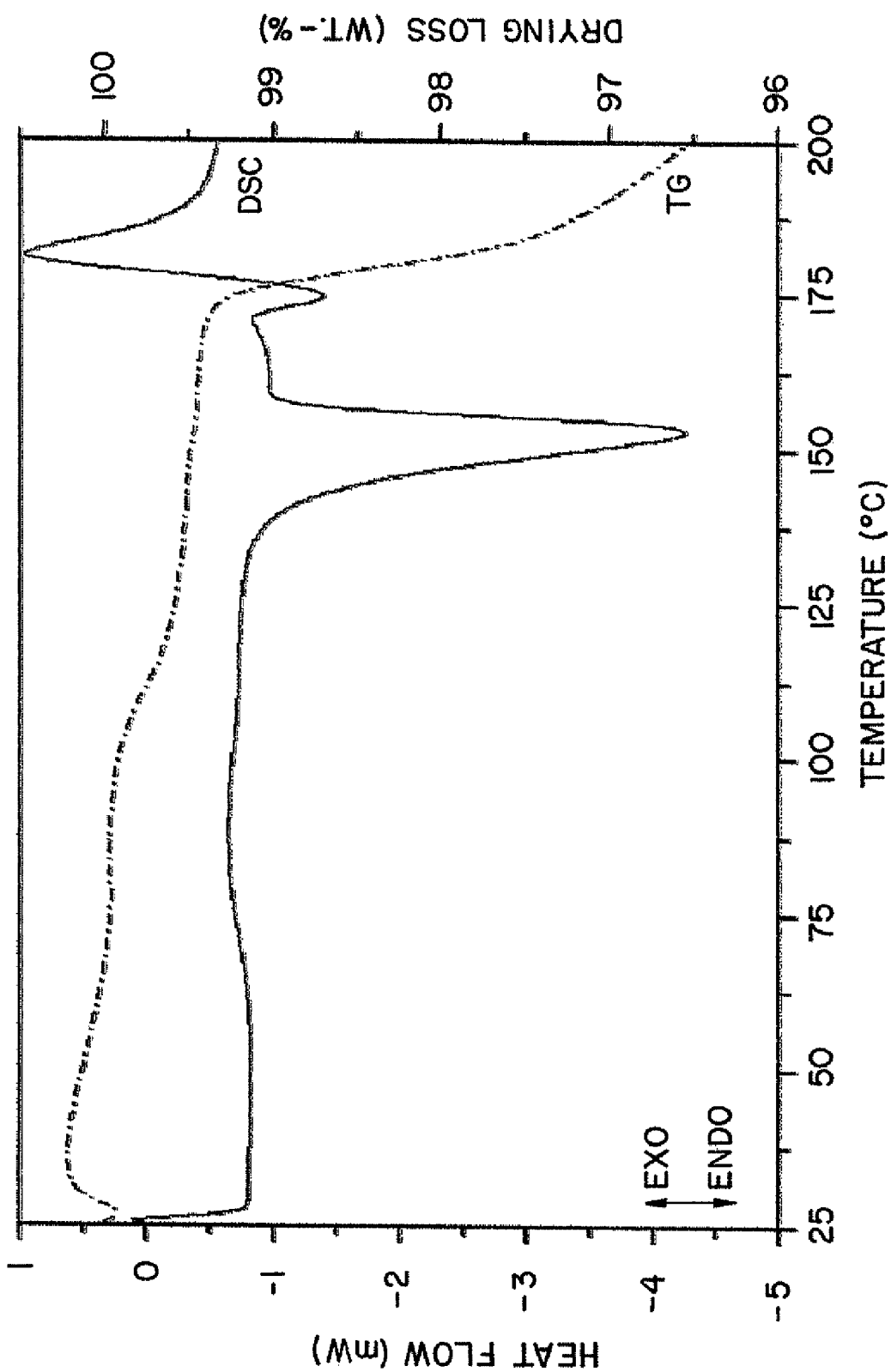

The melting points measured by DSC are stated in the Examples. The corresponding diagrams (FIGS. 4-6) can be found in the Appendix in the Figures section.

Figure 4:
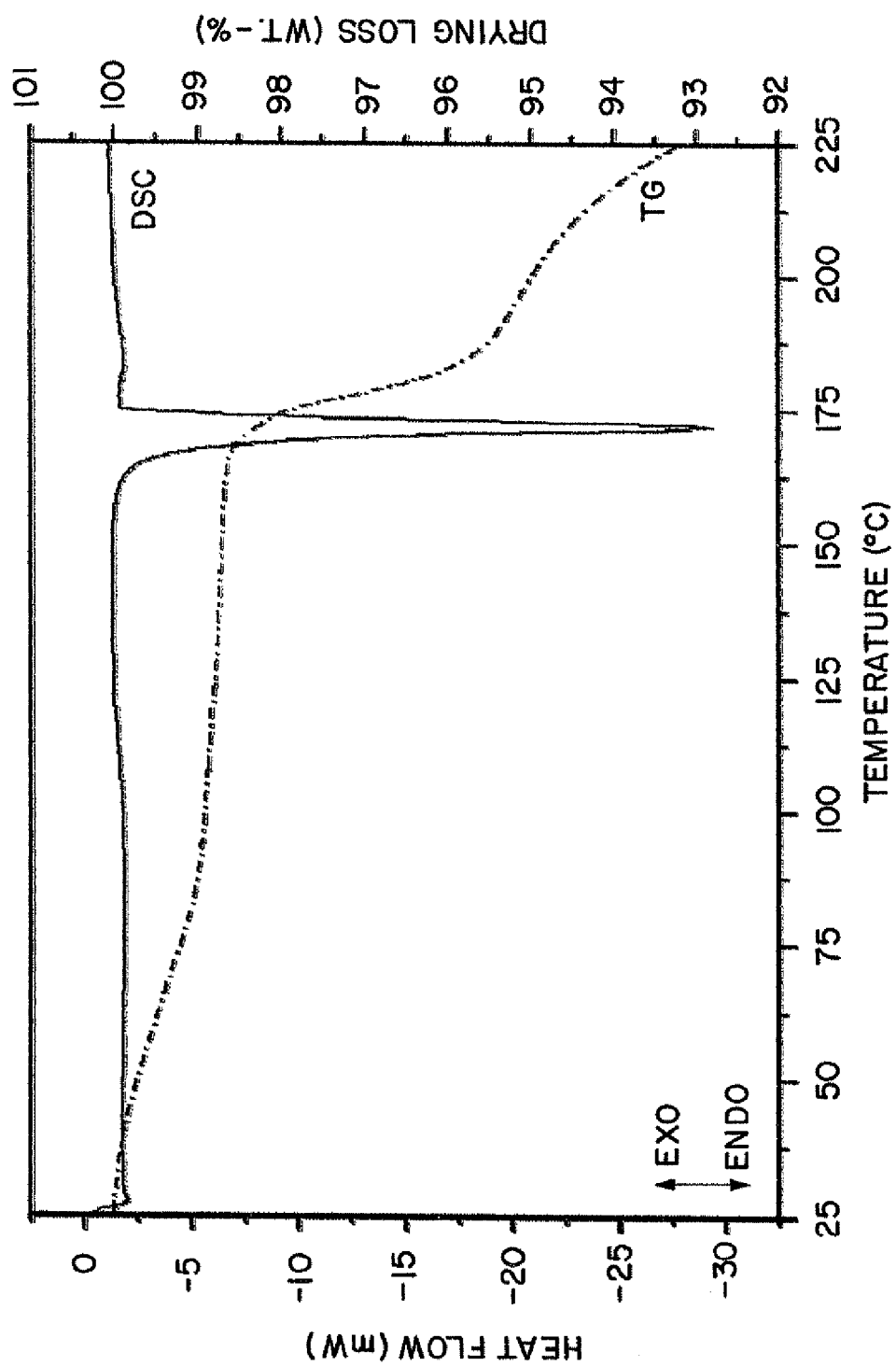

FIG. 4: DSC/TG diagram of the free base of N-(5-{(R)-2-[3-(4,4-diethyl-2-oxo-4H-benzo[d][1,3]oxazin-1-yl)-1,1-dimethyl-propylamino]-1-hydroxy-ethyl}-2-hydroxy-phenyl)-methanesulphonamide FIG. 5: DSC/TG diagram of the monohydrochloride of N-(5-{(R)-2-[3-(4,4-diethyl-2-oxo-4H-benzo[d][1,3]oxazin-1-yl)-1,1-dimethyl-propylamino]-1-hydroxy-ethyl}-2-hydroxy-phenyl)-methanesulphonamide FIG. 6: DSC/TG diagram of the monohydrobromide of N-(5-{(R)-2-[3-(4,4-diethyl-2-oxo-4H-benzo[d][1,3]oxazin-1-yl)-1,1-dimethyl-propylamino]-1-hydroxy-ethyl}-2-hydroxy-phenyl)-methanesulphonamide

COMBINATIONS

The compounds of formula 1 may be used on their own or in combination with other active substances of formula 1. If desired the compounds of formula 1 may also be used in combination with W, where W denotes a pharmacologically active substance and (for example) is selected from among the betamimetics, anticholinergics, corticosteroids, PDE4-inhibitors, LTD4-antagonists, EGFR-inhibitors, dopamine agonists, H1-antihistamines, PAF-antagonists and PI3-kinase inhibitors. Moreover, double or triple combinations of W may be combined with the compounds of formula 1. Combinations of W might be, for example:

W denotes a betamimetic, combined with an anticholinergic, corticosteroid, PDE4-inhibitor, EGFR-inhibitor or LTD4-antagonist, W denotes an anticholinergic, combined with a betamimetic, corticosteroid, PDE4-inhibitor, EGFR-inhibitor or LTD4-antagonist, W denotes a corticosteroid, combined with a PDE4-inhibitor, EGFR-inhibitor or LTD4-antagonist W denotes a PDE4-inhibitor, combined with an EGFR-inhibitor or LTD4-antagonist W denotes an EGFR-inhibitor, combined with an LTD4-antagonist.

The compounds used as betamimetics are preferably compounds selected from among albuterol, arformoterol, bambuterol, bitolterol, broxaterol, carbuterol, clenbuterol, fenoterol, formoterol, hexoprenaline, ibuterol, isoetharine, isoprenaline, levosalbutamol, mabuterol, meluadrine, metaproterenol, orciprenaline, pirbuterol, procaterol, reproterol, rimiterol, ritodrine, salmefamol, salmeterol, soterenol, sulphonterol, terbutaline, tiaramide, tolubuterol, zinterol, CHF-1035, HOKU-81, KUL-1248 and 3-(4-{6-[2-hydroxy-2-(4-hydroxy-3-hydroxymethyl-phenyl)-ethylamino]-hexyloxy}-butyl)-benzyl-sulphonamide 5-[2-(5.6-diethyl-indan-2-ylamino)-1-hydroxy-ethyl]-8-hydroxy-1H-quinoline-2-one 4-hydroxy-7-[2-{[2-{[3-(2-phenylethoxy)propyl] sulphonyl}ethyl]-amino}ethyl]-2(3H)-benzothiazolone 1-(2-fluoro-4-hydroxyphenyl)-2-[4-(1-benzimidazolyl)-2-methyl-2-butylamino]ethanol 1-[3-(4-methoxybenzyl-amino)-4-hydroxyphenyl]-2-[4-(1-benzimidazolyl)-2-methyl-2-butylamino]ethanol 1-[2H-5-hydroxy-3-oxo-4H-1,4-benzoxazin-8-yl]-2-[3-(4-N,N-dimethylaminophenyl)-2-methyl-2-propylamino] ethanol 1-[2H-5-hydroxy-3-oxo-4H-1,4-benzoxazin-8-yl]-2-[3-(4-methoxyphenyl)-2-methyl-2-propylamino]ethanol 1-[2H-5-hydroxy-3-oxo-4H-1,4-benzoxazin-8-yl]-2-[3-(4-n-butyloxyphenyl)-2-methyl-2-propylamino]ethanol 1-[2H-5-hydroxy-3-oxo-4H-1,4-benzoxazin-8-yl]-2-{4-[3-(4-methoxyphenyl)-1,2,4-triazole-3-yl]-2-methyl-2-butylamino}ethanol 5-hydroxy-8-(1-hydroxy-2-isopropylaminobutyl)-2H-1,4-benzoxazin-3-(4H)-on 1-(4-amino-3-chloro-5-trifluoromethylphenyl)-2-tert.-butylamino)ethanol 6-hydroxy-8-{1-hydroxy-2-[2-(4-methoxy-phenyl)-1,1-dimethyl-ethylamino]-ethyl}-4H-benzo[1,4]oxazin-3-one 6-hydroxy-8-{1-hydroxy-2-[2-(ethyl 4-phenoxy-acetate)-1,1-dimethyl-ethylamino]-ethyl}-4H-benzo[1,4]oxazin-3-one 6-hydroxy-8-{1-hydroxy-2-[2-(4-phenoxy-acetic acid)-1,1-dimethyl-ethylamino]-ethyl}-4H-benzo[1,4]oxazin-3-one 8-{2-[1,1-dimethyl-2-(2.4.6-trimethylphenyl)-ethylamino]-1-hydroxy-ethyl}-6-hydroxy-4H-benzo[1,4]oxazin-3-one 6-hydroxy-8-{1-hydroxy-2-[2-(4-hydroxy-phenyl)-1,1-dimethyl-ethylamino]-ethyl}-4H-benzo[1,4]oxazin-3-one 6-hydroxy-8-{1-hydroxy-2-[2-(4-isopropyl-phenyl)-1.1 dimethyl-ethylamino]-ethyl}-4H-benzo[1,4]oxazin-3-one 8-{2-[2-(4-ethyl-phenyl)-1,1-dimethyl-ethylamino]-1-hydroxy-ethyl}-6-hydroxy-4H-benzo[1,4]oxazin-3-one 8-{2-[2-(4-ethoxy-phenyl)-1,1-dimethyl-ethylamino]-1-hydroxy-ethyl}-6-hydroxy-4H-benzo[1,4]oxazin-3-one 4-(4-{2-[2-hydroxy-2-(6-hydroxy-3-oxo-3.4-dihydro-2H-benzo[1,4]oxazin-8-yl)-ethylamino]-2-methyl-propyl}-phenoxy)-butyric acid 8-{2-[2-(3.4-difluoro-phenyl)-1,1-dimethyl-ethylamino]-1-hydroxy-ethyl}-6-hydroxy-4H-benzo[1,4]oxazin-3-one 1-(4-ethoxy-carbonylamino-3-cyano-5-fluorophenyl)-2-(tert-butylamino)ethanol optionally in the form of the racemates, enantiomers, diastereomers thereof and optionally in the form of the pharmacologically acceptable acid addition salts, solvates or hydrates thereof. According to the invention the acid addition salts of the betamimetics are preferably selected from among the hydrochloride, hydrobromide, hydriodide, hydrosulphate, hydrophosphate, hydromethanesulphonate, hydronitrate, hydromaleate, hydroacetate, hydrocitrate, hydrofumarate, hydrotartrate, hydroxalate, hydrosuccinate, hydrobenzoate and hydro-p-toluenesulphonate.

The anticholinergics used are preferably compounds selected from among the tiotropium salts, preferably the bromide salt, oxitropium salts, preferably the bromide salt, flutropium salts, preferably the bromide salt, ipratropium salts, preferably the bromide salt, glycopyrronium salts, preferably the bromide salt, trospium salts, preferably the chloride salt, tolterodine. In the above-mentioned salts the cations are the pharmacologically active constituents. As anions the above-mentioned salts may preferably contain the chloride, bromide, iodide, sulphate, phosphate, methanesulphonate, nitrate, maleate, acetate, citrate, fumarate, tartrate, oxalate, succinate, benzoate or p-toluenesulphonate, while chloride, bromide, iodide, sulphate, methanesulphonate or p-toluenesulphonate are preferred as counter-ions. Of all the salts the chlorides, bromides, iodides and methanesulphonates are particularly preferred.

Other preferred anticholinergics are selected from among the salts of formula AC-1

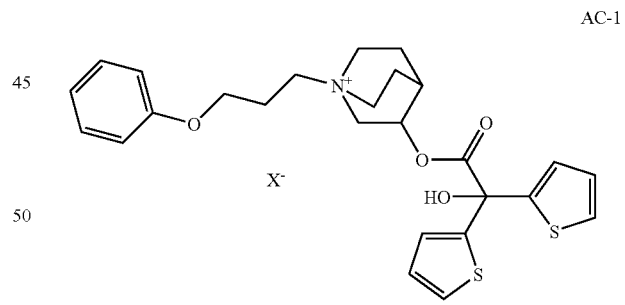

AC-1 wherein X⁻ denotes an anion with a single negative charge, preferably an anion selected from among the fluoride, chloride, bromide, iodide, sulphate, phosphate, methanesulphonate, nitrate, maleate, acetate, citrate, fumarate, tartrate, oxalate, succinate, benzoate and p-toluenesulphonate, preferably an anion with a single negative charge, particularly preferably an anion selected from among the fluoride, chloride, bromide, methanesulphonate and p-toluenesulphonate, particularly preferably bromide, optionally in the form of the racemates, enantiomers or hydrates thereof. Of particular importance are those pharmaceutical combinations which contain the enantiomers of formula AC-1-ene

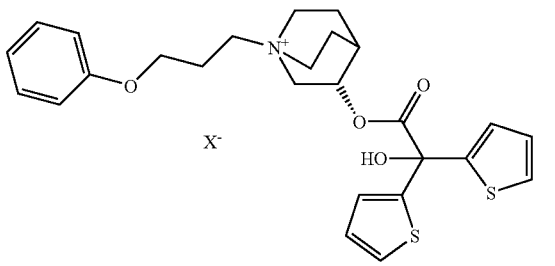

AC-1-ene wherein X⁻ may have the above-mentioned meanings. Other preferred anticholinergics are selected from the salts of formula AC-2

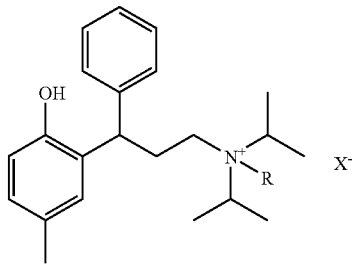

AC-2 wherein R denotes either methyl or ethyl and wherein X⁻ may have the above-mentioned meanings. In an alternative embodiment the compound of formula AC-2 may also be present in the form of the free base AC-2-base.

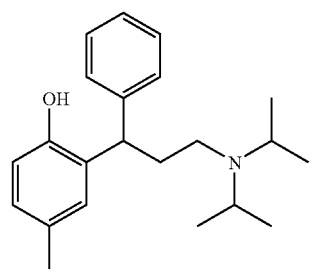

AC-2-base

Other specified compounds are:
tropenol 2,2-diphenylpropionate methobromide,
scopine 2,2-diphenylpropionate methobromide,
scopine 2-fluoro-2,2-diphenylacetate methobromide,
tropenol 2-fluoro-2,2-diphenylacetate methobromide;
tropenol 3,3',4,4'-tetrafluorobenzilate methobromide,
scopine 3,3',4,4'-tetrafluorobenzilate methobromide,
tropenol 4,4'-difluorobenzilate methobromide,
scopine 4,4'-difluorobenzilate methobromide,
tropenol 3,3'-difluorobenzilate methobromide,
scopine 3,3'-difluorobenzilate methobromide;
tropenol 9-hydroxy-fluorene-9-carboxylate methobromide;
tropenol 9-fluoro-fluorene-9-carboxylate methobromide;
scopine 9-hydroxy-fluorene-9-carboxylate methobromide;
scopine 9-fluoro-fluorene-9-carboxylate methobromide;
tropenol 9-methyl-fluorene-9-carboxylate methobromide;
scopine 9-methyl-fluorene-9-carboxylate methobromide;
cyclopropyltropine benzilate methobromide;
cyclopropyltropine 2,2-diphenylpropionate methobromide;
cyclopropyltropine 9-hydroxy-xanthene-9-carboxylate methobromide;
cyclopropyltropine 9-methyl-fluorene-9-carboxylate methobromide;
cyclopropyltropine 9-methyl-xanthene-9-carboxylate methobromide;
cyclopropyltropine 9-hydroxy-fluorene-9-carboxylate methobromide;
cyclopropyltropine methyl 4,4'-difluorobenzilate methobromide.
tropenol 9-hydroxy-xanthene-9-carboxylate methobromide;
scopine 9-hydroxy-xanthene-9-carboxylate methobromide;
tropenol 9-methyl-xanthene-9-carboxylate-methobromide;
scopine 9-methyl-xanthene-9-carboxylate-methobromide;
tropenol 9-ethyl-xanthene-9-carboxylate methobromide;
tropenol 9-difluoromethyl-xanthene-9-carboxylate methobromide;
scopine 9-hydroxymethyl-xanthene-9-carboxylate methobromide, The above-mentioned compounds may also be used as salts within the scope of the present invention, wherein instead of the methobromide the salts metho-X are used, wherein X may have the meanings given hereinbefore for X⁻.

As corticosteroids it is preferable to use compounds selected from among prednisolone, prednisone, butixocort propionate, flunisolide, beclomethasone, triamcinolone, budesonide, fluticasone, mometasone, ciclesonide, rofleponide, dexamethasone, betamethasone, deflazacort, RPR-106541, NS-126, ST-26 and
(S)-fluoromethyl 6,9-difluoro-17-[(2-furanylcarbonyl)oxy]-11-hydroxy-16-methyl-3-oxo-androsta-1,4-diene-17-carbothionate
(S)-(2-oxo-tetrahydro-furan-3S-yl)6,9-difluoro-11-hydroxy-16-methyl-3-oxo-17-propionyloxy-androsta-1,4-diene-17-carbothionate,
etiprednol-dichloroacetate optionally in the form of the racemates, enantiomers or diastereomers thereof and optionally in the form of the salts and derivatives thereof, the solvates and/or hydrates thereof. Any reference to steroids includes a reference to any salts or derivatives, hydrates or solvates thereof which may exist. Examples of possible salts and derivatives of the steroids may be: alkali metal salts, such as for example sodium or potassium salts, sulphobenzoates, phosphates, isonicotinates, acetates, propionates, dihydrogen phosphates, palmitates, pivalates or furoates.

PDE4-inhibitors which may be used are preferably compounds selected from among enprofyllin, theophyllin, roflumilast, ariflo (cilomilast), tofimilast, pumafentrin, lirimilast, arofyllin, atizoram, D-4418, Bay-198004, BY343, CP-325.366, D-4396 (Sch-351591), AWD-12-281 (GW-842470), NCS-613, CDP-840, D-4418, PD-168787, T-440, T-2585, V-11294A, CI-1018, CDC-801, CDC-3052, D-22888, YM-58997, Z-15370 and N-(3,5-dichloro-1-oxo-pyridin-4-yl)-4-difluoromethoxy-3-cyclopropylmethoxybenzamide (−)p-[(4aR*,10bS*)-9-ethoxy-1,2,3,4,4a,10b-hexahydro-8-methoxy-2-methylbenzo[s][1,6]naphthyridin-6-yl]-N,N-diisopropylbenzamide (R)-(+)-1-(4-bromobenzyl)-4-[(3-cyclopentyloxy)-4-methoxyphenyl]-2-pyrrolidone 3-(cyclopentyloxy-4-methoxyphenyl)-1-(4-N'-[N-2-cyano-S-methyl-isothioureido]benzyl)-2-pyrrolidone cis[4-cyano-4-(3-cyclopentyloxy-4-methoxyphenyl)cyclohexane-1-carboxylic acid]

2-carbomethoxy-4-cyano-4-(3-cyclopropylmethoxy-4-difluoromethoxy-phenyl)cyclohexan-1-one cis[4-cyano-4-(3-cyclopropylmethoxy-4-difluoromethoxyphenyl)cyclohexan-1-ol]

(R)-(+)-ethyl [4-(3-cyclopentyloxy-4-methoxyphenyl)pyrrolidin-2-ylidene]acetate (S)-(−)-ethyl [4-(3-cyclopentyloxy-4-methoxyphenyl)pyrrolidin-2-ylidene]acetate 9-cyclopentyl-5,6-dihydro-7-ethyl-3-(2-thienyl)-9H-pyrazolo[3.4-c]-1,2,4-triazolo[4.3-a]pyridine 9-cyclopentyl-5,6-dihydro-7-ethyl-3-(tert-butyl)-9H-pyrazolo[3.4-c]-1,2,4-triazolo[4.3-a]pyridine optionally in the form of the racemates, enantiomers or diastereomers thereof and optionally in the form of the pharmacologically acceptable acid addition salts thereof, the solvates and/or hydrates thereof. According to the invention the acid addition salts of the betamimetics are preferably selected from among the hydrochloride, hydrobromide, hydriodide, hydrosulphate, hydrophosphate, hydromethanesulphonate, hydronitrate, hydromaleate, hydroacetate, hydrocitrate, hydrofumarate, hydrotartrate, hydroxalate, hydrosuccinate, hydrobenzoate and hydro-p-toluenesulphonate.

The LTD4-antagonists used are preferably compounds selected from among montelukast, pranlukast, zafirlukast, MCC-847 (ZD-3523), MN-001, MEN-91507 (LM-1507), VUF-5078, VUF-K-8707, L-733321 and 1-(((R)-(3-(2-(6,7-difluoro-2-quinolinyl)ethenyl)phenyl)-3-(2-(2-hydroxy-2-propyl)phenyl)thio)methylcyclopropane-acetic acid, 1-(((1(R)-3(3-(2-(2,3-dichlorothieno[3,2-b]pyridin-5-yl)-(E)-ethenyl)phenyl)-3-(2-(1-hydroxy-1-methylethyl)phenyl)propyl)thio)methyl)cyclopropaneacetic acid

[2-[[2-(4-tert-butyl-2-thiazolyl)-5-benzofuranyl]oxymethyl]phenyl]acetic acid optionally in the form of the racemates, enantiomers or diastereomers thereof and optionally in the form of the pharmacologically acceptable acid addition salts, solvates and/or hydrates thereof. According to the invention the acid addition salts of the betamimetics are preferably selected from among the hydrochloride, hydrobromide, hydroiodide, hydrosulphate, hydrophosphate, hydromethanesulphonate, hydronitrate, hydromaleate, hydroacetate, hydrocitrate, hydrofumarate, hydrotartrate, hydroxalate, hydrosuccinate, hydrobenzoate and hydro-p-toluenesulphonate. By salts or derivatives which the LTD4-antagonists may optionally be capable of forming are meant, for example: alkali metal salts, such as for example sodium or potassium salts, alkaline earth metal salts, sulphobenzoates, phosphates, isonicotinates, acetates, propionates, dihydrogen phosphates, palmitates, pivalates or furoates. EGFR-inhibitors which may be used are preferably compounds selected from among cetuximab, trastuzumab, ABX-EGF, Mab ICR-62 and 4-[(3-chloro-4-fluorophenyl)amino]-6-{[4-(morpholin-4-yl)-1-oxo-2-buten-1-yl]-amino}-7-cyclopropylmethoxy-quinazoline 4-[(3-chloro-4-fluorophenyl)amino]-6-{[4-(N,N-diethylamino)-1-oxo-2-buten-1-yl]-amino}-7-cyclopropylmethoxy-quinazoline 4-[(3-chloro-4-fluorophenyl)amino]-6-{[4-(N,N-dimethylamino)-1-oxo-2-buten-1-yl]amino}-7-cyclopropylmethoxy-quinazoline 4-[(R)-(1-phenyl-ethyl)amino]-6-{[4-(morpholin-4-yl)-1-oxo-2-buten-1-yl]amino}-7-cyclopentyloxy-quinazoline 4-[(3-chloro-4-fluoro-phenyl)amino]-6-{[4-((R)-6-methyl-2-oxo-morpholin-4-yl)-1-oxo-2-buten-1-yl]amino}-7-cyclopropylmethoxy-quinazoline 4-[(3-chloro-4-fluoro-phenyl)amino]-6-{[4-((R)-6-methyl-2-oxo-morpholin-4-yl)-1-oxo-2-buten-1-yl]amino}-7-[(S)-(tetrahydrofuran-3-yl)oxy]-quinazoline 4-[(3-chloro-4-fluoro-phenyl)amino]-6-{[4-((R)-2-methoxymethyl-6-oxo-morpholin-4-yl)-1-oxo-2-buten-1-yl]amino}-7-cyclopropylmethoxy-quinazoline 4-[(3-chloro-4-fluoro-phenyl)amino]-6-[2-((S)-6-methyl-2-oxo-morpholin-4-yl)-ethoxy]-7-methoxy-quinazoline 4-[(3-chloro-4-fluorophenyl)amino]-6-({4-[N-(2-methoxyethyl)-N-methyl-amino]-1-oxo-2-buten-1-yl}amino)-7-cyclopropylmethoxy-quinazoline 4-[(3-chloro-4-fluorophenyl)amino]-6-{[4-(N,N-dimethylamino)-1-oxo-2-buten-1-yl]amino}-7-cyclopentyloxy-quinazoline 4-[(R)-(1-phenyl-ethyl)amino]-6-{[4-(N,N-bis-(2-methoxyethyl)-amino)-1-oxo-2-buten-1-yl]amino}-7-cyclopropylmethoxy-quinazoline 4-[(R)-(1-phenyl-ethyl)amino]-6-({4-[N-(2-methoxyethyl)-N-ethyl-amino]-1-oxo-2-buten-1-yl}amino)-7-cyclopropylmethoxy-quinazoline 4-[(R)-(1-phenyl-ethyl)amino]-6-({4-[N-(2-methoxyethyl)-N-methyl-amino]-1-oxo-2-buten-1-yl}amino)-7-cyclopropylmethoxy-quinazoline 4-[(R)-(1-phenyl-ethyl)amino]-6-({4-[N-(tetrahydropyran-4-yl)-N-methyl-amino]-1-oxo-2-buten-1-yl}amino)-7-cyclopropylmethoxy-quinazoline 4-[(3-chloro-4-fluorophenyl)amino]-6-{[4-(N,N-dimethylamino)-1-oxo-2-buten-1-yl]amino}-7-((R)-tetrahydrofuran-3-yloxy)-quinazoline 4-[(3-chloro-4-fluorophenyl)amino]-6-{[4-(N,N-dimethylamino)-1-oxo-2-buten-1-yl]amino}-7-((S)-tetrahydrofuran-3-yloxy)-quinazoline 4-[(3-chloro-4-fluorophenyl)amino]-6-({4-[N-(2-methoxyethyl)-N-methyl-amino]-1-oxo-2-buten-1-yl}amino)-7-cyclopentyloxy-quinazoline 4-[(3-chloro-4-fluorophenyl)amino]-6-{[4-(N-cyclopropyl-N-methyl-amino)-1-oxo-2-buten-1-yl]amino}-7-cyclopentyloxy-quinazoline 4-[(3-chloro-4-fluorophenyl)amino]-6-{[4-(N,N-dimethylamino)-1-oxo-2-buten-1-yl]amino}-7-[(R)-(tetrahydrofuran-2-yl)methoxy]-quinazoline 4-[(3-chloro-4-fluorophenyl)amino]-6-{[4-(N,N-dimethylamino)-1-oxo-2-buten-1-yl]amino}-7-[(S)-(tetrahydrofuran-2-yl)methoxy]-quinazoline 4-[(3-ethynyl-phenyl)amino]-6.7-bis-(2-methoxy-ethoxy)-quinazoline 4-[(3-chloro-4-fluorophenyl)amino]-7-[3-(morpholin-4-yl)-propyloxy]-6-[(vinyl-carbonyl)amino]-quinazoline 4-[(R)-(1-phenyl-ethyl)amino]-6-(4-hydroxy-phenyl)-7H-pyrrolo[2,3-d]pyrimidine 3-cyano-4-[(3-chloro-4-fluorophenyl)amino]-6-{[4-(N,N-dimethylamino)-1-oxo-2-buten-1-yl]amino}-7-ethoxyquinoline 4-{[3-chloro-4-(3-fluoro-benzyloxy)-phenyl]amino}-6-(5-{[(2-methanesulphonyl-ethyl)amino]methyl}-furan-2-yl)quinazoline 4-[(R)-(1-phenyl-ethyl)amino]-6-{[4-((R)-6-methyl-2-oxo-morpholin-4-yl)-1-oxo-2-buten-1-yl]amino}-7-methoxy-quinazoline 4-[(3-chloro-4-fluorophenyl)amino]-6-{[4-(morpholin-4-yl)-1-oxo-2-buten-1-yl]-amino}-7-[(tetrahydrofuran-2-yl)methoxy]-quinazoline 4-[(3-chloro-4-fluorophenyl)amino]-6-({4-[N,N-bis-(2-methoxy-ethyl)-amino]-1-oxo-2-buten-1-yl}amino)-7-[(tetrahydrofuran-2-yl)methoxy]-quinazoline 4-[(3-ethynyl-phenyl)amino]-6-{[4-(5.5-dimethyl-2-oxo-morpholin-4-yl)-1-oxo-2-buten-1-yl]amino}-quinazoline 4-[(3-chloro-4-fluoro-phenyl)amino]-6-[2-(2.2-dimethyl-6-oxo-morpholin-4-yl)-ethoxy]-7-methoxy-quinazoline 4-[(3-chloro-4-fluoro-phenyl)amino]-6-[2-(2.2-dimethyl-6-oxo-morpholin-4-yl)-ethoxy]-7-[(R)-(tetrahydrofuran-2-yl)methoxy]-quinazoline 4-[(3-chloro-4-fluoro-phenyl)amino]-7-[2-(2.2-dimethyl-6-oxo-morpholin-4-yl)-ethoxy]-6-[(S)-(tetrahydrofuran-2-yl)methoxy]-quinazoline 4-[(3-chloro-4-fluoro-phenyl)amino]-6-{2-[4-(2-oxo-morpholin-4-yl)-piperidin-1-yl]-ethoxy}-7-methoxy-quinazoline 4-[(3-chloro-4-fluoro-phenyl)amino]-6-[1-(tert.-butyloxycarbonyl)-piperidin-4-yloxy]-7-methoxy-quinazoline 4-[(3-chloro-4-fluoro-phenyl)amino]-6-(trans-4-amino-cyclohexan-1-yloxy)-7-methoxy-quinazoline 4-[(3-chloro-4-fluoro-phenyl)amino]-6-(trans-4-methanesulphonylamino-cyclohexan-1-yloxy)-7-methoxy-quinazoline 4-[(3-chloro-4-fluoro-phenyl)amino]-6-(tetrahydropyran-3-yloxy)-7-methoxy-quinazoline 4-[(3-chloro-4-fluoro-phenyl)amino]-6-(1-methyl-piperidin-4-yloxy)-7-methoxy-quinazoline 4-[(3-chloro-4-fluoro-phenyl)amino]-6-{1-[(morpholin-4-yl)carbonyl]-piperidin-4-yl-oxy}-7-methoxy-quinazoline 4-[(3-chloro-4-fluoro-phenyl)amino]-6-{1-[(methoxymethyl)carbonyl]-piperidin-4-yl-oxy}-7-methoxy-quinazoline 4-[(3-chloro-4-fluoro-phenyl)amino]-6-(piperidin-3-yloxy)-7-methoxy-quinazoline 4-[(3-chloro-4-fluoro-phenyl)amino]-6-[1-(2-acetylamino-ethyl)-piperidin-4-yloxy]-7-methoxy-quinazoline 4-[(3-chloro-4-fluoro-phenyl)amino]-6-(tetrahydropyran-4-yloxy)-7-ethoxy-quinazoline 4-[(3-chloro-4-fluoro-phenyl)amino]-6-((S)-tetrahydrofuran-3-yloxy)-7-hydroxy-quinazoline 4-[(3-chloro-4-fluoro-phenyl)amino]-6-(tetrahydropyran-4-yloxy)-7-(2-methoxy-ethoxy)-quinazoline 4-[(3-chloro-4-fluoro-phenyl)amino]-6-{trans-4-[(dimethylamino)sulphonylamino]-cyclohexan-1-yloxy}-7-methoxy-quinazoline 4-[(3-chloro-4-fluoro-phenyl)amino]-6-{trans-4-[(morpholin-4-yl)carbonylamino]-cyclohexan-1-yloxy}-7-methoxy-quinazoline 4-[(3-chloro-4-fluoro-phenyl)amino]-6-{trans-4-[(morpholin-4-yl)sulphonylamino]-cyclohexan-1-yloxy}-7-methoxy-quinazoline 4-[(3-chloro-4-fluoro-phenyl)amino]-6-(tetrahydropyran-4-yloxy)-7-(2-acetylamino-ethoxy)-quinazoline 4-[(3-chloro-4-fluoro-phenyl)amino]-6-(tetrahydropyran-4-yloxy)-7-(2-methanesulphonylamino-ethoxy)-quinazoline 4-[(3-chloro-4-fluoro-phenyl)amino]-6-{1-[(piperidin-1-yl)carbonyl]-piperidin-4-yloxy}-7-methoxy-quinazoline 4-[(3-chloro-4-fluoro-phenyl)amino]-6-(1-aminocarbonylmethyl-piperidin-4-yloxy)-7-methoxy-quinazoline 4-[(3-chloro-4-fluoro-phenyl)amino]-6-(cis-4-{N-[(tetrahydropyran-4-yl)carbonyl]-N-methyl-amino}-cyclohexan-1-yloxy)-7-methoxy-quinazoline 4-[(3-chloro-4-fluoro-phenyl)amino]-6-(cis-4-{N-[(morpholin-4-yl)carbonyl]-N-methyl-amino}-cyclohexan-1-yloxy)-7-methoxy-quinazoline 4-[(3-chloro-4-fluoro-phenyl)amino]-6-(cis-4-{N-[(morpholin-4-yl)sulphonyl]-N-methyl-amino}-cyclohexan-1-yloxy)-7-methoxy-quinazoline 4-[(3-chloro-4-fluoro-phenyl)amino]-6-(trans-4-ethansulphonylamino-cyclohexan-1-yloxy)-7-methoxy-quinazoline 4-[(3-chloro-4-fluoro-phenyl)amino]-6-(1-methanesulphonyl-piperidin-4-yloxy)-7-ethoxy-quinazoline 4-[(3-chloro-4-fluoro-phenyl)amino]-6-(1-methanesulphonyl-piperidin-4-yloxy)-7-(2-methoxy-ethoxy)-quinazoline 4-[(3-chloro-4-fluoro-phenyl)amino]-6-[1-(2-methoxy-acetyl)-piperidin-4-yloxy]-7-(2-methoxy-ethoxy)-quinazoline 4-[(3-chloro-4-fluoro-phenyl)amino]-6-(cis-4-acetylamino-cyclohexan-1-yloxy)-7-methoxy-quinazoline 4-[(3-ethynyl-phenyl)amino]-6-[1-(tert.-butyloxycarbonyl)-piperidin-4-yloxy]-7-methoxy-quinazoline 4-[(3-ethynyl-phenyl)amino]-6-(tetrahydropyran-4-yloxy]-7-methoxy-quinazoline 4-[(3-chloro-4-fluoro-phenyl)amino]-6-(cis-4-{N-[(piperidin-1-yl)carbonyl]-N-methyl-amino}-cyclohexan-1-yloxy)-7-methoxy-quinazoline 4-[(3-chloro-4-fluoro-phenyl)amino]-6-(cis-4-{N-[(4-methyl-piperazin-1-yl)carbonyl]-N-methyl-amino}-cyclohexan-1-yloxy)-7-methoxy-quinazoline 4-[(3-chloro-4-fluoro-phenyl)amino]-6-{cis-4-[(morpholin-4-yl)carbonylamino]-cyclohexan-1-yloxy}-7-methoxy-quinazoline 4-[(3-chloro-4-fluoro-phenyl)amino]-6-{1-[2-(2-oxopyrrolidin-1-yl)ethyl]-piperidin-4-yloxy}-7-methoxy-quinazoline 4-[(3-chloro-4-fluoro-phenyl)amino]-6-{1-[(morpholin-4-yl)carbonyl]-piperidin-4-yloxy}-7-(2-methoxy-ethoxy)-quinazoline 4-[(3-ethynyl-phenyl)amino]-6-(1-acetyl-piperidin-4-yloxy)-7-methoxy-quinazoline 4-[(3-ethynyl-phenyl)amino]-6-(1-methyl-piperidin-4-yloxy)-7-methoxy-quinazoline 4-[(3-ethynyl-phenyl)amino]-6-(1-methanesulphonyl-piperidin-4-yloxy)-7-methoxy-quinazoline 4-[(3-chloro-4-fluoro-phenyl)amino]-6-(1-methyl-piperidin-4-yloxy)-7(2-methoxy-ethoxy)-quinazoline 4-[(3-chloro-4-fluoro-phenyl)amino]-6-(1-isopropyloxycarbonyl-piperidin-4-yloxy)-7-methoxy-quinazoline 4-[(3-chloro-4-fluoro-phenyl)amino]-6-(cis-4-methylamino-cyclohexan-1-yloxy)-7-methoxy-quinazoline 4-[(3-chloro-4-fluoro-phenyl)amino]-6-{cis-4-[N-(2-methoxy-acetyl)-N-methyl-amino]-cyclohexan-1-yloxy}-7-methoxy-quinazoline 4-[(3-ethynyl-phenyl)amino]-6-(piperidin-4-yloxy)-7-methoxy-quinazoline 4-[(3-ethynyl-phenyl)amino]-6-[1-(2-methoxy-acetyl)-piperidin-4-yloxy]-7-methoxy-quinazoline 4-[(3-ethynyl-phenyl)amino]-6-{1-[(morpholin-4-yl)carbonyl]-piperidin-4-yloxy}-7-methoxy-quinazoline 4-[(3-chloro-4-fluoro-phenyl)amino]-6-{1-[(cis-2,6-dimethyl-morpholin-4-yl)carbonyl]-piperidin-4-yloxy}-7-methoxy-quinazoline 4-[(3-chloro-4-fluoro-phenyl)amino]-6-{1-[(2-methyl-morpholin-4-yl)carbonyl]-piperidin-4-yloxy}-7-methoxy-quinazoline 4-[(3-chloro-4-fluoro-phenyl)amino]-6-{1-[(S,S)-(2-oxa-5-aza-bicyclo[2,2,1]hept-5-yl)carbonyl]-piperidin-4-yloxy}-7-methoxy-quinazoline 4-[(3-chloro-4-fluoro-phenyl)amino]-6-{1-[(N-methyl-N-2-methoxyethyl-amino)carbonyl]-piperidin-4-yloxy}-7-methoxy-quinazoline 4-[(3-chloro-4-fluoro-phenyl)amino]-6-(1-ethyl-piperidin-4-yloxy)-7-methoxy-quinazoline 4-[(3-chloro-4-fluoro-phenyl)amino]-6-{1-[(2-methoxy-ethyl)carbonyl]-piperidin-4-yloxy}-7-methoxy-quinazoline 4-[(3-chloro-4-fluoro-phenyl)amino]-6-{1-[(3-methoxypropyl-amino)-carbonyl]-piperidin-4-yloxy}-7-methoxy-quinazoline 4-[(3-chloro-4-fluoro-phenyl)amino]-6-[cis-4-(N-methanesulphonyl-N-methyl-amino)-cyclohexan-1-yloxy]-7-methoxy-quinazoline 4-[(3-chloro-4-fluoro-phenyl)amino]-6-[cis-4-(N-acetyl-N-methyl-amino)-cyclohexan-1-yloxy]-7-methoxy-quinazoline 4-[(3-chloro-4-fluoro-phenyl)amino]-6-(trans-4-methylamino-cyclohexan-1-yloxy)-7-methoxy-quinazoline 4-[(3-chloro-4-fluoro-phenyl)amino]-6-[trans-4-(N-methanesulphonyl-N-methyl-amino)-cyclohexan-1-yloxy]-7-methoxy-quinazoline 4-[(3-chloro-4-fluoro-phenyl)amino]-6-(trans-4-dimethylamino-cyclohexan-1-yloxy)-7-methoxy-quinazoline 4-[(3-chloro-4-fluoro-phenyl)amino]-6-(trans-4-{N-[(morpholin-4-yl)carbonyl]-N-methyl-amino}-cyclohexan-1-yloxy)-7-methoxy-quinazoline 4-[(3-chloro-4-fluoro-phenyl)amino]-6-[2-(2.2-dimethyl-6-oxo-morpholin-4-yl)-ethoxy]-7-[(S)-(tetrahydrofuran-2-yl)methoxy]-quinazoline 4-[(3-chloro-4-fluoro-phenyl)amino]-6-(1-methanesulphonyl-piperidin-4-yloxy)-7-methoxy-quinazoline 4-[(3-chloro-4-fluoro-phenyl)amino]-6-(1-cyano-piperidin-4-yloxy)-7-methoxy-quinazoline optionally in the form of the racemates, enantiomers, diastereomers thereof and optionally in the form of the pharmacologically acceptable acid addition salts, solvates or hydrates thereof. According to the invention the preferred acid addition salts of the betamimetics are selected from among the hydrochloride, hydrobromide, hydriodide, hydrosulphate, hydrophosphate, hydromethanesulphonate, hydronitrate, hydromaleate, hydroacetate, hydrocitrate, hydrofumarate, hydrotartrate, hydroxalate, hydrosuccinate, hydrobenzoate and hydro-p-toluenesulphonate.

The dopamine agonists used are preferably compounds selected from among bromocriptin, cabergoline, alpha-dihydroergocryptine, lisuride, pergolide, pramipexol, roxindol, ropinirol, talipexol, tergurid and viozan, optionally in the form of the racemates, enantiomers, diastereomers thereof and optionally in the form of the pharmacologically acceptable acid addition salts, solvates or hydrates thereof. According to the invention the preferred acid addition salts of the betamimetics are selected from among the hydrochloride, hydrobromide, hydriodide, hydrosulphate, hydrophosphate, hydromethanesulphonate, hydronitrate, hydromaleate, hydroacetate, hydrocitrate, hydrofumarate, hydrotartrate, hydrooxalate, hydrosuccinate, hydrobenzoate and hydro-p-toluenesulphonate.

H1-Antihistamines which may be used are preferably compounds selected from among epinastine, cetirizine, azelastine, fexofenadine, levocabastine, loratadine, mizolastine, ketotifen, emedastine, dimetindene, clemastine, bamipine, cexchlorpheniramine, pheniramine, doxylamine, chlorophenoxamine, dimenhydrinate, diphenhydramine, promethazine, ebastine, desloratidine and meclozine, optionally in the form of the racemates, enantiomers, diastereomers thereof and optionally in the form of the pharmacologically acceptable acid addition salts, solvates or hydrates thereof. According to the invention the preferred acid addition salts of the betamimetics are selected from among the hydrochloride, hydrobromide, hydriodide, hydrosulphate, hydrophosphate, hydromethanesulphonate, hydronitrate, hydromaleate, hydroacetate, hydrocitrate, hydrofumarate, hydrotartrate, hydroxalate, hydrosuccinate, hydrobenzoate and hydro-p-toluenesulphonate.

The PAF-antagonists used are preferably compounds selected from among 4-(2-chlorophenyl)-9-methyl-2-[3(4-morpholinyl)-3-propanon-1-yl]-6H-thieno-[3,2-f]-[1,2,4]triazolo[4,3-a][1,4]diazepine 6-(2-chlorophenyl)-8,9-dihydro-1-methyl-8-[(4-morpholinyl)carbonyl]-4H,7H-cyclo-penta-[4,5]thieno-[3,2-f][1,2,4]triazolo[4,3-a][1,4]diazepine, optionally in the form of the racemates, enantiomers, diastereomers thereof and optionally in the form of the pharmacologically acceptable acid addition salts, solvates or hydrates thereof. According to the invention the preferred acid addition salts of the betamimetics are selected from among the hydrochloride, hydrobromide, hydriodide, hydrosulphate, hydrophosphate, hydromethanesulphonate, hydronitrate, hydromaleate, hydroacetate, hydrocitrate, hydrofumarate, hydrotartrate, hydroxalate, hydrosuccinate, hydrobenzoate and hydro-p-toluenesulphonate.

FORMULATIONS

Suitable formulations for administering the compounds of formula 1 include for example tablets, capsules, suppositories, solutions, powders etc. The content of the pharmaceutically active compound(s) should be in the range from 0.05 to 90 wt.-%, preferably 0.1 to 50 wt.-% of the composition as a whole. Suitable tablets may be obtained, for example, by mixing the active substance(s) with known excipients, for example inert diluents such as calcium carbonate, calcium phosphate or lactose, disintegrants such as corn starch or alginic acid, binders such as starch or gelatine, lubricants such as magnesium stearate or talc and/or agents for delaying release, such as carboxymethyl cellulose, cellulose acetate phthalate, or polyvinyl acetate. The tablets may also comprise several layers.

Coated tablets may be prepared accordingly by coating cores produced analogously to the tablets with substances normally used for tablet coatings, for example collidone or shellac, gum arabic, talc, titanium dioxide or sugar. To achieve delayed release or prevent incompatibilities the core may also consist of a number of layers. Similarly the tablet coating may consist of a number of layers to achieve delayed release, possibly using the excipients mentioned above for the tablets.

Syrups containing the active substances or combinations thereof according to the invention may additionally contain a sweetener such as saccharine, cyclamate, glycerol or sugar and a flavour enhancer, e.g. a flavouring such as vanilline or orange extract. They may also contain suspension adjuvants or thickeners such as sodium carboxymethyl cellulose, wetting agents such as, for example, condensation products of fatty alcohols with ethylene oxide, or preservatives such as p-hydroxybenzoates.

Solutions are prepared in the usual way, e.g. with the addition of isotonic agents, preservatives such as p-hydroxybenzoates or stabilisers such as alkali metal salts of ethylenediaminetetraacetic acid, optionally using emulsifiers and/or dispersants, while if water is used as diluent, for example, organic solvents may optionally be used as solubilisers or dissolving aids, and the solutions may be transferred into injection vials or ampoules or infusion bottles.

Capsules containing the compounds of formula 1 according to the invention may for example be prepared by mixing the active substances with inert carriers such as lactose or sorbitol and packing them into gelatine capsules. Suitable suppositories may be made for example by mixing with carriers provided for this purpose, such as neutral fats or polyethyleneglycol or the derivatives thereof. Excipients which may be used include, for example, water, pharmaceutically acceptable organic solvents such as paraffins (e.g. petroleum fractions), vegetable oils (e.g. groundnut or sesame oil), mono- or polyfunctional alcohols (e.g. ethanol or glycerol), carriers such as e.g. natural mineral powders (e.g. kaolins, clays, talc, chalk), synthetic mineral powders (e.g. highly dispersed silicic acid and silicates), sugars (e.g. cane sugar, lactose and glucose), emulsifiers (e.g. lignin, spent sulphite liquors, methylcellulose, starch and polyvinylpyrrolidone) and lubricants (e.g. magnesium stearate, talc, stearic acid and sodium lauryl sulphate).

For oral use the tablets may obviously contain, in addition to the carriers specified, additives such as sodium citrate, calcium carbonate and dicalcium phosphate together with various additional substances such as starch, preferably potato starch, gelatine and the like. Lubricants such as magnesium stearate, sodium laurylsulphate and talc may also be used to produce the tablets. In the case of aqueous suspensions the active substances may be combined with various flavour enhancers or colourings in addition to the abovementioned excipients.

In the preferred use of the compounds of formula 1 for the treatment of respiratory complaints it is particularly preferred according to the invention to use preparations or pharmaceutical formulations which can be administered by inhalation. Inhalable preparations include inhalable powders, propellant-containing metered-dose aerosols or propellant-free inhalable solutions. Within the scope of the present invention, the term propellant-free inhalable solutions also includes concentrates or sterile ready-to-use inhalable solutions.

The compounds of formula 1 which are particularly preferably used in crystalline form according to the invention are preferably used to prepare powders for inhalation. The inhalable powders which may be used according to the invention may contain the crystalline compounds of formula 1 either on their own or in admixture with suitable physiologically acceptable excipients.

If the active substances are present in admixture with physiologically acceptable excipients, the following physiologically acceptable excipients may be used to prepare these inhalable powders according to the invention: monosaccharides (e.g. glucose or arabinose), disaccharides (e.g. lactose, saccharose, maltose), oligo- and polysaccharides (e.g. dextrans), polyalcohols (e.g. sorbitol, mannitol, xylitol), salts (e.g. sodium chloride, calcium carbonate) or mixtures of these excipients. Preferably, mono- or disaccharides are used, while the use of lactose or glucose is preferred, particularly, but not exclusively, in the form of their hydrates. For the purposes of the invention, lactose is the particularly preferred excipient, while lactose monohydrate is most particularly preferred.

Within the scope of the inhalable powders according to the invention the excipients have a maximum average particle size of up to 250 μm, preferably between 10 and 150 μm, most preferably between 15 and 80 μm. In some cases it may seem appropriate to add finer excipient fractions with an average particle size of 1 to 9 μm to the excipients mentioned above. These finer excipients are also selected from the group of possible excipients listed hereinbefore. Finally, in order to prepare the inhalable powders according to the invention, micronised active substance, preferably with an average particle size of 0.5 to 10 μm, more preferably from 1 to 5 μm, is added to the excipient mixture. Processes for producing the inhalable powders according to the invention by grinding and micronising and finally mixing the ingredients together are known from the prior art.

The inhalable powders according to the invention may be administered using inhalers known from the prior art.

The inhalation aerosols containing propellant gas according to the invention may contain the active substance dissolved in the propellant gas or in dispersed form. The propellant gases which may be used to prepare the inhalation aerosols are known from the prior art. Suitable propellant gases are selected from among hydrocarbons such as n-propane, n-butane or isobutane and halohydrocarbons such as fluorinated derivatives of methane, ethane, propane, butane, cyclopropane or cyclobutane. The above-mentioned propellant gases may be used on their own or in admixture. Particularly preferred propellant gases are halogenated alkane derivatives selected from TG134a and TG227 and mixtures thereof.

The propellant-driven inhalation aerosols may also contain other ingredients such as co-solvents, stabilisers, surfactants, antioxidants, lubricants and pH adjusters. All these ingredients are known in the art.

The propellant-driven inhalation aerosols mentioned above may be administered using inhalers known in the art (MDIs=metered dose inhalers).

The dosage of the compounds according to the invention is naturally highly dependent on the method of administration and the complaint which is being treated. When administered by inhalation the compounds of the formula are characterised by a high potency even at doses in the μg range. The compounds of the formula may also be used effectively above the μg range. The dosage may then be in the milligram range, for example.

In another aspect the present invention relates to the above-mentioned pharmaceutical formulations as such, which are characterised in that they contain a compound of formula 1, particularly preferably the above-mentioned pharmaceutical formulations administered by inhalation.

The following examples of formulations illustrate the present invention without restricting its scope:

Examples of Pharmaceutical Formulations

| A) Tablets | per tablet |
|---|---|
| active substance | 100 mg |
| lactose | 140 mg |
| corn starch | 240 mg |
| polyvinylpyrrolidone | 15 mg |
| magnesium stearate | 5 mg |
| | 500 mg |

The finely ground active substance, lactose and some of the corn starch are mixed together. The mixture is screened, then moistened with a solution of polyvinylpyrrolidone in water, kneaded, wet-granulated and dried. The granules, the remaining corn starch and the magnesium stearate are screened and mixed together. The mixture is compressed to produce tablets of suitable shape and size.

| B) | Tablets | per tablet |
|---|---|---|
| | active substance | 80 mg |
| | corn starch | 190 mg |
| | lactose | 55 mg |
| | microcrystalline cellulose | 35 mg |
| | polyvinylpyrrolidone | 15 mg |
| | sodium-carboxymethyl starch | 23 mg |
| | magnesium stearate | 2 mg |
| | | 400 mg |

The finely ground active substance, some of the corn starch, lactose, microcrystalline cellulose and polyvinylpyrrolidone are mixed together, the mixture is screened and worked with the remaining corn starch and water to form a granulate which is dried and screened. The sodium carboxymethyl starch and the magnesium stearate are added and mixed in and the mixture is compressed to form tablets of a suitable size.

| C) | Coated tablets | per coated tablet |
|---|---|---|
| | Active substance | 5 mg |
| | Corn starch | 41.5 mg |
| | Lactose | 30 mg |
| | Polyvinylpyrrolidone | 3 mg |
| | Magnesium stearate | 0.5 mg |
| | | 80 mg |

The active substance, corn starch, lactose and polyvinylpyrrolidone are thoroughly mixed and moistened with water. The moist mass is pushed through a screen with a 1 mm mesh size, dried at about 45° C. and the granules are then passed through the same screen. After the magnesium stearate has been mixed in, convex tablet cores with a diameter of 6 mm are compressed in a tablet-making machine. The tablet cores thus produced are coated in known manner with a covering consisting essentially of sugar and talc. The finished coated tablets are polished with wax.

| D) | Capsules | per capsule |
|---|---|---|
| | Active substance | 50 mg |
| | Corn starch | 268.5 mg |
| | Magnesium stearate | 1.5 mg |
| | | 320 mg |

The substance and corn starch are mixed and moistened with water. The moist mass is screened and dried. The dry granules are screened and mixed with magnesium stearate. The finished mixture is packed into size 1 hard gelatine capsules.

| E) | Ampoule solution | |
|---|---|---|
| | active substance | 50 mg |
| | sodium chloride | 50 mg |
| | water for inj. | 5 ml |

The active substance is dissolved in water at its own pH or optionally at pH 5.5 to 6.5 and sodium chloride is added to make it isotonic. The solution obtained is filtered free from pyrogens and the filtrate is transferred under aseptic conditions into ampoules which are then sterilised and sealed by fusion. The ampoules contain 5 mg, 25 mg and 50 mg of active substance.

| F) | Suppositories | |
|---|---|---|
| | Active substance | 50 mg |
| | Solid fat | 1650 mg |
| | | 1700 mg |

The hard fat is melted. At 40° C. the ground active substance is homogeneously dispersed therein. It is cooled to 38° C. and poured into slightly chilled suppository moulds.

| G) | Oral suspension | |
|---|---|---|
| | active substance | 50 mg |
| | hydroxyethylcellulose | 50 mg |
| | sorbic acid | 5 mg |
| | sorbitol (70%) | 600 mg |
| | glycerol | 200 mg |
| | flavouring | 15 mg |
| | water ad | 5 ml |

Distilled water is heated to 70° C. Hydroxyethyl-cellulose is dissolved therein with stirring. After the addition of sorbitol solution and glycerol the preparation is cooled to ambient temperature. At ambient temperature the sorbic acid, flavouring and substance are added. The suspension is evacuated with stirring to eliminate any air.

The invention claimed is:
1. Solvent-free, crystalline forms of an enantiomer of a compound of formula 1-base

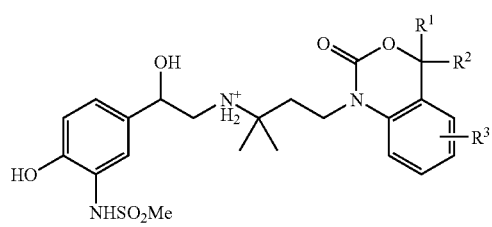

1-base wherein
$R^1$ and $R^2$ which may be identical or different, denote ethyl or propyl, or together denote —$CH_2$—$CH_2$—, —$CH_2$—$CH_2$—$CH_2$—, —$CH_2$—$CH_2$—$CH_2$—$CH_2$— or —$CH_2$—$CH_2$—$CH_2$—$CH_2$—$CH_2$— and R³ denotes hydrogen, fluorine, chlorine, OH, methyl, ethyl, methoxy or ethoxy.

2. Solvent-free, crystalline forms of an enantiomer of a compound of formula 1-base according to claim 1, wherein R¹ and R² are identical.

3. Solvent-free, crystalline forms of an enantiomer of a compound of formula 1-base according to claim 1, wherein
R¹ and R² which may be identical or different, denote ethyl or propyl, or together denote —CH₂—CH₂, —CH₂—CH₂—CH₂—CH₂ or —CH₂—CH₂—CH₂—CH₂—CH₂—

R³ denotes hydrogen, fluorine, OH, methyl or methoxy.

4. Solvent-free, crystalline forms of an enantiomer of a compound of formula 1-base according to claim 3, wherein R¹ and R² identical.

5. Solvent-free, crystalline forms of an enantiomer of a compound of formula 1-base according to claim 3, wherein R³ denotes hydrogen.

6. Solvent-free, crystalline forms of an enantiomer of a compound according to claim 1 of formula:
- 1.7-base-N-(5-{2-[1,1-dimethyl-3-(2-oxo-4,4-dipropyl-4H-benzo[d][1,3]oxazin-1-yl)-propylamino]-1-hydroxy-ethyl}-2-hydroxy-phenyl)-methanesulphonamide;
- 1.8-base-N-[5-(2-{1,1-dimethyl-3-[spiro(cyclohexane-1.4'-2H-3',1'-benzoxazin)-2'-oxo-1-yl]-propylamino}1-1-hydroxy-ethyl)-2-hydroxy-phenyl]-methanesulphonamide;
- 1.9-base-N-[5-(2-{1,1-dimethyl-3-[spiro(cyclopropyl-1,4'-2H-3',1'-benzoxazin)-2'-oxo-1-yl]-propylamino}1-hydroxy-ethyl)-2-hydroxy-phenyl]-methanesulphonamide;
- 1.10-base-N-(5-{2-[3-(4,4-diethyl-2-oxo-4H-benzo[d][1,3]oxazin-1-yl)-1,1-dimethyl-propylamino]-1-hydroxy-ethyl}-2-hydroxy-phenyl)-methanesulphonamide;
- 1.11-base-N-(5-{2-[3-(4,4-diethyl-6-fluoro-2-oxo-4H-benzo[d][1,3]oxazin-1-yl)-1,1-dimethyl-propylamino]-1-hydroxy-ethyl}-2-hydroxy-phenyl)-methanesulphonamide;
- 1.12-base-N-(5-{2-[3-(4,4-diethyl-7-fluoro-2-oxo-4H-benzo[d][1,3]oxazin-1-yl)-1,1-dimethyl-propylamino]-1-hydroxy-ethyl}-2-hydroxy-phenyl)-methanesulphonamide;
- 1.13-base-N-(5-{2-[3-(4,4-diethyl-8-methoxy-2-oxo-4H-benzo[d][1,3]oxazin-1-yl)-1,1-dimethyl-propylamino]-1-hydroxy-ethyl}-2-hydroxy-phenyl)-methanesulphonamide; or
- 1.14-base-N-(5-{2-[3-(4,4-diethyl-6-methoxy-2-oxo-4H-benzo[d][1,3]oxazin-1-yl)-1,1-dimethyl-propylamino]-1-hydroxy-ethyl}-2-hydroxy-phenyl)-methanesulphonamide.

7. Solvent-free, crystalline forms of an enantiomer of a compound according to claim 1, wherein said compound is N-(5-{(R)-2-[3-(4,4-diethyl-2-oxo-4H-benzo[d][1,3]oxazin-1-yl)-1,1-dimethyl-propylamino]-1-hydroxy-ethyl}-2-hydroxy-phenyl)-methanesulphonamide.

8. Crystalline compound according to claim 7, wherein said crystalline compound has an endothermic maximum at 168° C.

9. Crystalline compound according to claim 7, wherein said crystalline compound has X-ray reflections at d=18.56 Å, 8.14 Å and 6.31 Å.

10. The enantiomer of claim 1, wherein said enantiomer is the R-enantiomer.

11. The enantiomer of claim 2, wherein said enantiomer is the R-enantiomer.

12. The enantiomer of claim 3, wherein said enantiomer is the R-enantiomer.

13. The enantiomer of claim 4, wherein said enantiomer is the R-enantiomer.

14. The enantiomer of claim 5, wherein said enantiomer is the R-enantiomer.

15. The enantiomer of claim 6, wherein said enantiomer is the R-enantiomer.

16. The enantiomer of claim 7, wherein said enantiomer is the R-enantiomer.

* * * * *